US012569653B2

(12) United States Patent
Halstead et al.

(10) Patent No.: US 12,569,653 B2
(45) Date of Patent: Mar. 10, 2026

(54) BALLOON CATHETERS AND METHODS OF MANUFACTURE AND USE

(71) Applicant: Embolx, Inc., Sunnyvale, CA (US)

(72) Inventors: Greg Halstead, Sunnyvale, CA (US); Michael P. Allen, Los Altos, CA (US)

(73) Assignee: Embolx, Inc., Sunnyvale, CA (US)

( * ) Notice: Subject to any disclaimer, the term of this patent is extended or adjusted under 35 U.S.C. 154(b) by 0 days.

(21) Appl. No.: 17/938,559

(22) Filed: Oct. 6, 2022

(65) Prior Publication Data

US 2023/0211131 A1     Jul. 6, 2023

Related U.S. Application Data

(63) Continuation of application No. 16/545,519, filed on Aug. 20, 2019, now Pat. No. 11,464,948, which is a continuation-in-part of application No. PCT/US2019/035966, filed on Jun. 7, 2019, and a continuation-in-part of application No. 16/047,922, (Continued)

(51) Int. Cl.
| | |
|---|---|
| *A61M 25/10* | (2013.01) |
| *A61M 5/00* | (2006.01) |
| *A61M 25/00* | (2006.01) |

(52) U.S. Cl.
CPC ........ *A61M 25/1006* (2013.01); *A61M 5/007* (2013.01); *A61M 25/005* (2013.01); *A61M 25/1025* (2013.01); *A61M 25/1029* (2013.01); *A61M 2025/0004* (2013.01); *A61M 2025/0042* (2013.01); *A61M 25/0043* (2013.01); *A61M*

*2025/105* (2013.01); *A61M 2025/1061* (2013.01); *A61M 2025/1075* (2013.01); *A61M 2025/1093* (2013.01)

(58) Field of Classification Search
CPC .............. A61M 25/10; A61M 25/1006; A61M 25/1025; A61M 25/1034; A61M 25/104; A61M 2025/1061; A61M 2025/1093
See application file for complete search history.

(56) References Cited

U.S. PATENT DOCUMENTS

| | | | |
|---|---|---|---|
| 3,734,100 A | 5/1973 | Walker et al. | |
| 4,198,981 A | 4/1980 | Sinnreich | |
| | (Continued) | | |

FOREIGN PATENT DOCUMENTS

| | | | |
|---|---|---|---|
| CN | 101400400 A | 4/2009 | |
| CN | 102159277 A | 8/2011 | |
| | (Continued) | | |

OTHER PUBLICATIONS

Angiodynamics; Soft-vu angiographic catheters; 2 pages; retrieved from the internet (http://www.angiodynamics.com/products/soft-vu) on Aug. 17, 2018.

(Continued)

*Primary Examiner* — Kami A Bosworth
(74) *Attorney, Agent, or Firm* — Shay Glenn LLP

(57)     ABSTRACT

Balloon catheters that includes inner and outer elongate shafts, each of which is secured relative to an end of an inflatable member. The inner and outer elongate shafts are secured relative to one another at one more discrete connection locations. The balloon bonding locations are disposed radially inward relative to an outer dimension of the outer elongate shaft.

27 Claims, 18 Drawing Sheets

Related U.S. Application Data filed on Jul. 27, 2018, now Pat. No. 12,268,824, said application No. PCT/US2019/035966 is a continuation of application No. 16/004,247, filed on Jun. 8, 2018, now Pat. No. 10,350,382, said application No. 16/545,519 is a continuation-in-part of application No. 15/413,262, filed on Jan. 23, 2017, now Pat. No. 10,786,660, which is a continuation of application No. 15/044,864, filed on Feb. 16, 2016, now Pat. No. 9,550,046.

(56) References Cited

U.S. PATENT DOCUMENTS

| | | | |
|---|---|---|---|
| 4,545,390 A | 10/1985 | Leary |
| 4,581,017 A | 4/1986 | Sahota |
| 4,737,153 A | 4/1988 | Shimamura et al. |
| 4,748,982 A | 6/1988 | Horzewski et al. |
| 4,892,519 A | 1/1990 | Songer et al. |
| 4,896,669 A | 1/1990 | Bhate et al. |
| 4,898,591 A | 2/1990 | Jang et al. |
| 4,909,252 A | 3/1990 | Goldberger |
| 4,944,745 A | 7/1990 | Sogard et al. |
| 4,976,690 A | 12/1990 | Solar et al. |
| 4,990,143 A | 2/1991 | Sheridan |
| 5,000,734 A | 3/1991 | Boussignac et al. |
| 5,040,548 A | 8/1991 | Yock |
| 5,045,072 A | 9/1991 | Castillo et al. |
| 5,047,045 A | 9/1991 | Arney et al. |
| 5,078,685 A | 1/1992 | Colliver |
| 5,090,958 A | 2/1992 | Sahota |
| 5,100,386 A | 3/1992 | Inoue |
| 5,129,887 A | 7/1992 | Eutheneuer et al. |
| 5,137,513 A | 8/1992 | Mcinnes et al. |
| 5,156,594 A | 10/1992 | Keith et al. |
| 5,217,434 A | 6/1993 | Arney |
| 5,234,416 A | 8/1993 | Macaulay et al. |
| 5,254,107 A | 10/1993 | Soltesz |
| 5,279,562 A | 1/1994 | Sirhan et al. |
| 5,318,532 A | 6/1994 | Frassica |
| 5,334,154 A | 8/1994 | Samson et al. |
| 5,342,386 A | 8/1994 | Trotta |
| 5,356,388 A | 10/1994 | Sepetka et al. |
| 5,358,493 A | 10/1994 | Schweich, Jr. et al. |
| 5,370,655 A | 12/1994 | Burns |
| 5,380,301 A | 1/1995 | Prichard et al. |
| 5,423,754 A | 6/1995 | Cornelius et al. |
| 5,423,829 A | 6/1995 | Pham et al. |
| 5,429,605 A | 7/1995 | Richling |
| 5,454,795 A | 10/1995 | Samson |
| 5,470,314 A | 11/1995 | Walinsky |
| 5,484,409 A | 1/1996 | Atkinson et al. |
| 5,498,251 A | 3/1996 | Dalton |
| 5,501,667 A | 3/1996 | Verduin |
| 5,509,910 A | 4/1996 | Lunn |
| 5,538,510 A | 7/1996 | Fontirroche et al. |
| 5,556,383 A | 9/1996 | Wang et al. |
| 5,582,619 A | 12/1996 | Ken |
| 5,584,821 A | 12/1996 | Hobbs et al. |
| 5,588,442 A | 12/1996 | Scovil et al. |
| 5,599,326 A | 2/1997 | Carter |
| 5,624,449 A | 4/1997 | Pham et al. |
| 5,637,086 A | 6/1997 | Ferguson et al. |
| 5,643,254 A | 7/1997 | Scheldrup et al. |
| 5,647,198 A | 7/1997 | Mihailovic |
| 5,649,949 A | 7/1997 | Wallace et al. |
| 5,658,263 A | 8/1997 | Dang et al. |
| 5,669,905 A | 9/1997 | Scheldrup et al. |
| 5,674,198 A | 10/1997 | Leone |
| 5,690,666 A | 11/1997 | Berenstein et al. |
| 5,690,667 A | 11/1997 | Gia |
| 5,718,711 A | 2/1998 | Berenstein et al. |
| 5,722,424 A | 3/1998 | Engelson |
| 5,749,837 A | 5/1998 | Palermo et al. |
| 5,766,192 A | 6/1998 | Zacca |
| 5,769,830 A | 6/1998 | Parker |
| 5,775,327 A | 7/1998 | Randolph et al. |
| 5,792,300 A | 8/1998 | Inderbitzen et al. |
| 5,797,874 A | 8/1998 | Spears |
| 5,800,454 A | 9/1998 | Jacobsen et al. |
| 5,807,355 A | 9/1998 | Ramzipoor et al. |
| 5,820,592 A | 10/1998 | Hammerslag |
| 5,830,182 A | 11/1998 | Wang et al. |
| 5,833,705 A | 11/1998 | Ken et al. |
| 5,843,032 A | 12/1998 | Kastenhofer |
| 5,843,050 A | 12/1998 | Jones et al. |
| 5,851,203 A | 12/1998 | Van Muiden |
| 5,853,418 A | 12/1998 | Ken et al. |
| 5,868,704 A | 2/1999 | Campbell et al. |
| 5,879,324 A | 3/1999 | von Hoffmann |
| 5,891,110 A | 4/1999 | Larson et al. |
| 5,891,128 A | 4/1999 | Gia et al. |
| 5,911,717 A | 6/1999 | Jacobsen et al. |
| 5,938,653 A | 8/1999 | Pepin |
| 5,951,539 A | 9/1999 | Nita et al. |
| 5,951,929 A | 9/1999 | Wilson |
| 5,984,878 A | 11/1999 | Engelson |
| 5,984,929 A | 11/1999 | Bashiri et al. |
| 6,013,084 A | 1/2000 | Ken et al. |
| 6,014,919 A | 1/2000 | Jacobsen et al. |
| 6,019,757 A | 2/2000 | Scheldrup |
| 6,022,340 A | 2/2000 | Sepetka et al. |
| 6,036,670 A | 3/2000 | Wijeratne et al. |
| 6,036,682 A | 3/2000 | Lange et al. |
| 6,056,719 A | 5/2000 | Mickley |
| 6,066,157 A | 5/2000 | Barbere |
| 6,066,667 A | 5/2000 | Ashbrook |
| 6,068,610 A | 5/2000 | Ellis et al. |
| 6,071,286 A | 6/2000 | Mawad |
| 6,090,099 A | 7/2000 | Samson et al. |
| 6,103,037 A | 8/2000 | Wilson |
| 6,123,714 A | 9/2000 | Gia et al. |
| 6,156,061 A | 12/2000 | Wallace et al. |
| 6,165,163 A | 12/2000 | Chien et al. |
| 6,187,027 B1 | 2/2001 | Mariant et al. |
| 6,190,358 B1 | 2/2001 | Fitzmaurice et al. |
| 6,190,393 B1 | 2/2001 | Bevier et al. |
| 6,203,547 B1 | 3/2001 | Nguyen et al. |
| 6,258,080 B1 | 7/2001 | Samson |
| 6,270,495 B1 | 8/2001 | Palermo |
| 6,280,457 B1 | 8/2001 | Wallace et al. |
| 6,287,301 B1 | 9/2001 | Thompson et al. |
| 6,319,228 B1 | 11/2001 | Kastenhofer |
| 6,344,041 B1 | 2/2002 | Kupiecki et al. |
| 6,397,850 B1 | 6/2002 | Scheldrup et al. |
| 6,423,085 B1 | 7/2002 | Murayama et al. |
| 6,428,489 B1 | 8/2002 | Jacobsen et al. |
| 6,440,088 B1 | 8/2002 | Jacobsen et al. |
| 6,450,987 B1 | 9/2002 | Kramer |
| 6,468,266 B1 | 10/2002 | Bashiri et al. |
| 6,471,673 B1 | 10/2002 | Kastenhofer |
| 6,508,804 B2 | 1/2003 | Sarge et al. |
| 6,553,880 B2 | 4/2003 | Jacobsen et al. |
| 6,575,959 B1 | 6/2003 | Sarge et al. |
| 6,579,246 B2 | 6/2003 | Jacobsen et al. |
| 6,635,069 B1 | 10/2003 | Teoh et al. |
| 6,638,245 B2 | 10/2003 | Miller et al. |
| 6,648,874 B2 | 11/2003 | Parisi et al. |
| 6,652,508 B2 | 11/2003 | Griffin et al. |
| 6,656,550 B1 | 12/2003 | Zamore |
| 6,702,782 B2 | 3/2004 | Miller et al. |
| 6,702,802 B1 | 3/2004 | Hancock et al. |
| 6,706,025 B2 | 3/2004 | Engelson et al. |
| 6,733,459 B1 | 5/2004 | Atsurni |
| 6,766,720 B1 | 7/2004 | Jacobsen et al. |
| 6,780,181 B2 | 8/2004 | Kroll et al. |
| 6,835,189 B2 | 12/2004 | Musbach et al. |
| 6,849,062 B2 | 2/2005 | Kantor |
| 6,860,893 B2 | 3/2005 | Wallace et al. |
| 6,860,899 B1 | 3/2005 | Rivelli |
| 6,878,151 B2 | 4/2005 | Carrison et al. |
| 6,921,410 B2 | 7/2005 | Porter |
| 6,936,055 B1 | 8/2005 | Ken et al. |
| 6,997,937 B2 | 2/2006 | Jacobsen et al. |

(56)                    References Cited

U.S. PATENT DOCUMENTS

| | | | |
|---|---|---|---|
| 7,004,962 B2 | 2/2006 | Stinson | |
| 7,037,330 B1 | 5/2006 | Rivelli et al. | |
| 7,060,083 B2 | 6/2006 | Gerberding | |
| 7,070,607 B2 | 7/2006 | Murayama et al. | |
| 7,144,407 B1 | 12/2006 | Lasersohn | |
| 7,153,323 B1 | 12/2006 | Teoh et al. | |
| 7,166,122 B2 | 1/2007 | Aganon et al. | |
| 7,294,137 B2 | 11/2007 | Rivelli et al. | |
| 7,332,689 B2 | 2/2008 | Mertens et al. | |
| 7,412,285 B2 | 8/2008 | Schroeppel et al. | |
| 7,468,070 B2 | 12/2008 | Henry et al. | |
| 7,481,800 B2 | 1/2009 | Jacques | |
| 7,621,904 B2 | 11/2009 | McFerran et al. | |
| 7,645,259 B2 | 1/2010 | Goldman | |
| 7,654,979 B2 | 2/2010 | Simpson | |
| 7,742,811 B2 | 6/2010 | Schroeppel et al. | |
| 7,780,626 B2 | 8/2010 | Wu et al. | |
| 7,892,201 B1 | 2/2011 | Laguna et al. | |
| 7,942,847 B2 | 5/2011 | Stupecky et al. | |
| 7,998,165 B2 | 8/2011 | Huffmaster | |
| 8,066,667 B2 | 11/2011 | Hayman et al. | |
| 8,092,508 B2 | 1/2012 | Leynov et al. | |
| 8,202,292 B2 | 6/2012 | Kellett | |
| 8,206,373 B2 | 6/2012 | Zhou | |
| 8,348,890 B2 | 1/2013 | Gerrans et al. | |
| 8,961,550 B2 | 2/2015 | Lenker et al. | |
| 9,005,163 B2 | 4/2015 | Bonnette et al. | |
| 9,174,020 B2 | 11/2015 | Allen et al. | |
| 9,205,226 B2 | 12/2015 | Allen et al. | |
| 9,427,550 B2 | 8/2016 | Dakin et al. | |
| 9,550,046 B1 | 1/2017 | Allen | |
| 9,555,165 B2 | 1/2017 | Phan | |
| 9,844,383 B2 | 12/2017 | Allen | |
| 10,086,174 B2 | 10/2018 | Crall et al. | |
| 10,130,762 B2 | 11/2018 | Allen | |
| 10,350,382 B1 | 7/2019 | Halstead et al. | |
| 10,667,822 B2 | 6/2020 | Allen | |
| 10,780,252 B2 | 9/2020 | Allen et al. | |
| 10,786,660 B2 | 9/2020 | Allen et al. | |
| 11,123,482 B2 | 9/2021 | Allen | |
| 11,464,948 B2 | 10/2022 | Halstead et al. | |
| 2001/0008451 A1 | 7/2001 | Ishii et al. | |
| 2001/0041862 A1 | 11/2001 | Glickman | |
| 2002/0004666 A1 | 1/2002 | Schwager et al. | |
| 2002/0032457 A1 | 3/2002 | Sirhan et al. | |
| 2002/0193820 A1 | 12/2002 | Wakuda et al. | |
| 2003/0008726 A1 | 1/2003 | Sano | |
| 2003/0050600 A1 | 3/2003 | Ressemann et al. | |
| 2003/0114878 A1 | 6/2003 | Diederich et al. | |
| 2003/0125713 A1 | 7/2003 | McGlinch et al. | |
| 2003/0144657 A1 | 7/2003 | Bowe et al. | |
| 2003/0180488 A1 | 9/2003 | Lim et al. | |
| 2003/0191435 A1* | 10/2003 | Shkolnik | A61M 25/1034 |
| | | | 604/103 |
| 2003/0199914 A1 | 10/2003 | Diaz | |
| 2003/0220628 A1 | 11/2003 | Kilsch et al. | |
| 2004/0015151 A1 | 1/2004 | Chambers | |
| 2004/0073158 A1 | 4/2004 | Shah et al. | |
| 2004/0167415 A1 | 8/2004 | Gelfand et al. | |
| 2005/0131453 A1 | 6/2005 | Parodi | |
| 2005/0267407 A1 | 12/2005 | Goldman | |
| 2006/0106413 A1 | 5/2006 | Bence et al. | |
| 2006/0149186 A1 | 7/2006 | Wantink et al. | |
| 2006/0276886 A1 | 12/2006 | George et al. | |
| 2007/0055301 A1 | 3/2007 | Campbell et al. | |
| 2007/0088380 A1 | 4/2007 | Hirszowicz et al. | |
| 2007/0137651 A1 | 6/2007 | Glassenberg et al. | |
| 2007/0149927 A1 | 6/2007 | Itou et al. | |
| 2007/0197956 A1 | 8/2007 | Le et al. | |
| 2008/0033372 A1 | 2/2008 | Briscoe et al. | |
| 2008/0045908 A1 | 2/2008 | Gould et al. | |
| 2008/0208118 A1 | 8/2008 | Goldman | |
| 2008/0262470 A1 | 10/2008 | Lee et al. | |
| 2009/0131831 A1 | 5/2009 | Wright et al. | |
| 2009/0156999 A1 | 6/2009 | Adams et al. | |

| | | | |
|---|---|---|---|
| 2009/0177183 A1 | 7/2009 | Pinkernell et al. | |
| 2010/0030200 A1 | 2/2010 | Strauss et al. | |
| 2010/0113939 A1 | 5/2010 | Mashimo et al. | |
| 2010/0222637 A1 | 9/2010 | Kassab | |
| 2010/0249491 A1 | 9/2010 | Farnan et al. | |
| 2011/0098671 A1 | 4/2011 | Duffy et al. | |
| 2012/0203173 A1 | 8/2012 | Davies et al. | |
| 2012/0253447 A1 | 10/2012 | Hayasaka et al. | |
| 2013/0116651 A1 | 5/2013 | Takagi et al. | |
| 2013/0131610 A1 | 5/2013 | Dewaele et al. | |
| 2013/0261545 A1 | 10/2013 | Osypka | |
| 2014/0163421 A1 | 6/2014 | Van Hoven | |
| 2014/0371718 A1 | 12/2014 | Alvarez et al. | |
| 2015/0112255 A1 | 4/2015 | Jensen et al. | |
| 2015/0351729 A1 | 12/2015 | Chin et al. | |
| 2016/0008585 A1 | 1/2016 | Tano | |
| 2016/0067444 A1 | 3/2016 | Allen et al. | |
| 2016/0096002 A1 | 4/2016 | Di Caprio et al. | |
| 2016/0101261 A1 | 4/2016 | Kugler et al. | |
| 2016/0199067 A1 | 7/2016 | Smith et al. | |
| 2016/0213893 A1 | 7/2016 | Franklin | |
| 2017/0049495 A1 | 2/2017 | Yu et al. | |
| 2017/0095646 A1 | 4/2017 | Norman et al. | |
| 2017/0113025 A1 | 4/2017 | Chanduszko et al. | |
| 2017/0252542 A1 | 9/2017 | Iwano et al. | |
| 2017/0303890 A1 | 10/2017 | Yamashita | |
| 2018/0015248 A1 | 1/2018 | Logan et al. | |
| 2018/0056036 A1 | 3/2018 | Wada et al. | |
| 2018/0071484 A1 | 3/2018 | Raab et al. | |
| 2020/0030577 A1 | 1/2020 | Halstead et al. | |
| 2020/0297351 A1 | 9/2020 | Allen | |
| 2022/0296864 A1 | 9/2022 | Halstead et al. | |

FOREIGN PATENT DOCUMENTS

| | | | |
|---|---|---|---|
| CN | 102802698 A | 11/2012 | |
| CN | 102805893 A | 12/2012 | |
| CN | 103298517 A | 9/2013 | |
| CN | 103764217 A | 4/2014 | |
| CN | 103987421 A | 8/2014 | |
| CN | 105228684 A | 1/2016 | |
| CN | 105246537 A | 1/2016 | |
| CN | 105854151 A | 8/2016 | |
| CN | 106422033 A | 2/2017 | |
| DE | 102009025347 A1 | 12/2010 | |
| DE | 202011003097 U1 | 7/2011 | |
| EP | 0520692 A1 | 12/1992 | |
| EP | 1121955 A2 | 8/2001 | |
| EP | 1131126 B1 | 8/2004 | |
| EP | 2389968 A2 | 11/2011 | |
| EP | 3132823 A1 | 2/2017 | |
| GB | 2512696 A | 10/2014 | |
| JP | H03-207376 A | 9/1991 | |
| JP | H05-015604 A | 1/1993 | |
| JP | H06-277296 A | 10/1994 | |
| JP | H07-213617 A | 8/1995 | |
| JP | H10244006 A | 9/1998 | |
| JP | 2003500121 A | 1/2003 | |
| JP | 2005511108 A | 4/2005 | |
| JP | 2006511271 A | 4/2006 | |
| JP | 2007319468 A | 12/2007 | |
| JP | 2008522716 A | 7/2008 | |
| JP | 2008544801 A | 12/2008 | |
| JP | 2011087971 A | 5/2011 | |
| JP | 2011152181 A | 8/2011 | |
| JP | 201290779 A | 5/2012 | |
| JP | 2015523884 A | 8/2015 | |
| JP | 2016517778 A | 6/2016 | |
| KR | 20100006710 U | 7/2010 | |
| WO | WO89/08471 A1 | 9/1989 | |
| WO | WO99/48548 A1 | 9/1999 | |
| WO | WO00/32264 A1 | 6/2000 | |
| WO | WO2004/107965 A2 | 12/2004 | |
| WO | WO2007/121005 A1 | 10/2007 | |
| WO | WO2012/009486 A2 | 1/2012 | |
| WO | WO2012/099979 A1 | 7/2012 | |
| WO | WO2014/008489 A1 | 1/2014 | |

(56)                    References Cited

FOREIGN PATENT DOCUMENTS

WO      WO2017/142941  A1      8/2017
WO      WO2019/236951  A1     12/2019
WO      WO2020/023889  A1      1/2020

OTHER PUBLICATIONS

BMI ESPICOM Pharmaceutical and Medical Device News; Business Monitor Online: Vascular solutions expands complex intervention offerings with turnpike LP catheter; newsleter; 2pages; retrieved from the internet (https://dialog.proquest.com/professional/docview/1753127273?accountid=157282) on Apr. 18, 2018 (Abstract Only).
Cliffton et al.; Technique for visualization and perfusion of bronchial arteries: suggested clinical and diagnostic applications; Cancer; 16; pp. 444-452; Apr. 1963.
Cook Medical; Flexor technology; 16 pages; retrieved from the internet (https: cookmedical.com/data/resources/PI-BM-KCF-EN-201302_WEB.pdf) on May 5, 2019.
Matsuda et al.; Electrospinning fabrication of high-trackable catheter tip with gradually graded or gradient flexibility; J. Biomed. Mater. Res. B Appl. Biomater.; 1(35); pp. 35-41 doi: 10.1002/jbm.b.31061; (Abstract Only); Oct. 2008.
Nordson Medical; Extruded tubing technical information; 7 pages; retrieved from the internet (https://www.nordsonmedical.com/Components-and-Technologies/Medical-Tubing/Extruded-Tubing/Technical-Information/) on Aug. 17, 2018.
Rousselot et al.; Selective concentration of anticancer drugs in the liver: Hepatic-artery infusion and induced hepatic outflow block; JAMA; 191(9); pp. 707-710; Mar. 1965.
Vante Plasticweld Systems; Bonds and welds; 13 pages; retrieved from the internet (https://cathetertipping.com/home/our-products/bonding/) on Aug. 17, 2018.
Worldwide Videotex; Angiodynamics PCTA balloon catheter gets FDA market clearance; Biotech Equipment Update 5.9: N/A. Worldwide Videotex; Sep. 1, 1997; 2 pages; retrieved from the internet (https://dialog.proquest.com/professional/docview/680080033?accountid=157282) on Apr. 18, 2018 (Abstract Only).
Zeus; FluoroPEELZ peelable heat shrink; 9 pages; retrieved from the internet (https://www.zeusinc.com/products/heat-shrinkable-tubing/fluoropeelz-peelable-heat-shrink) on Aug. 17, 2018.
Roewer et al.; U.S. Appl. No. 18/043,873 entitled "Catheters adapted for agent delivery," filed Mar. 2, 2023.

* cited by examiner

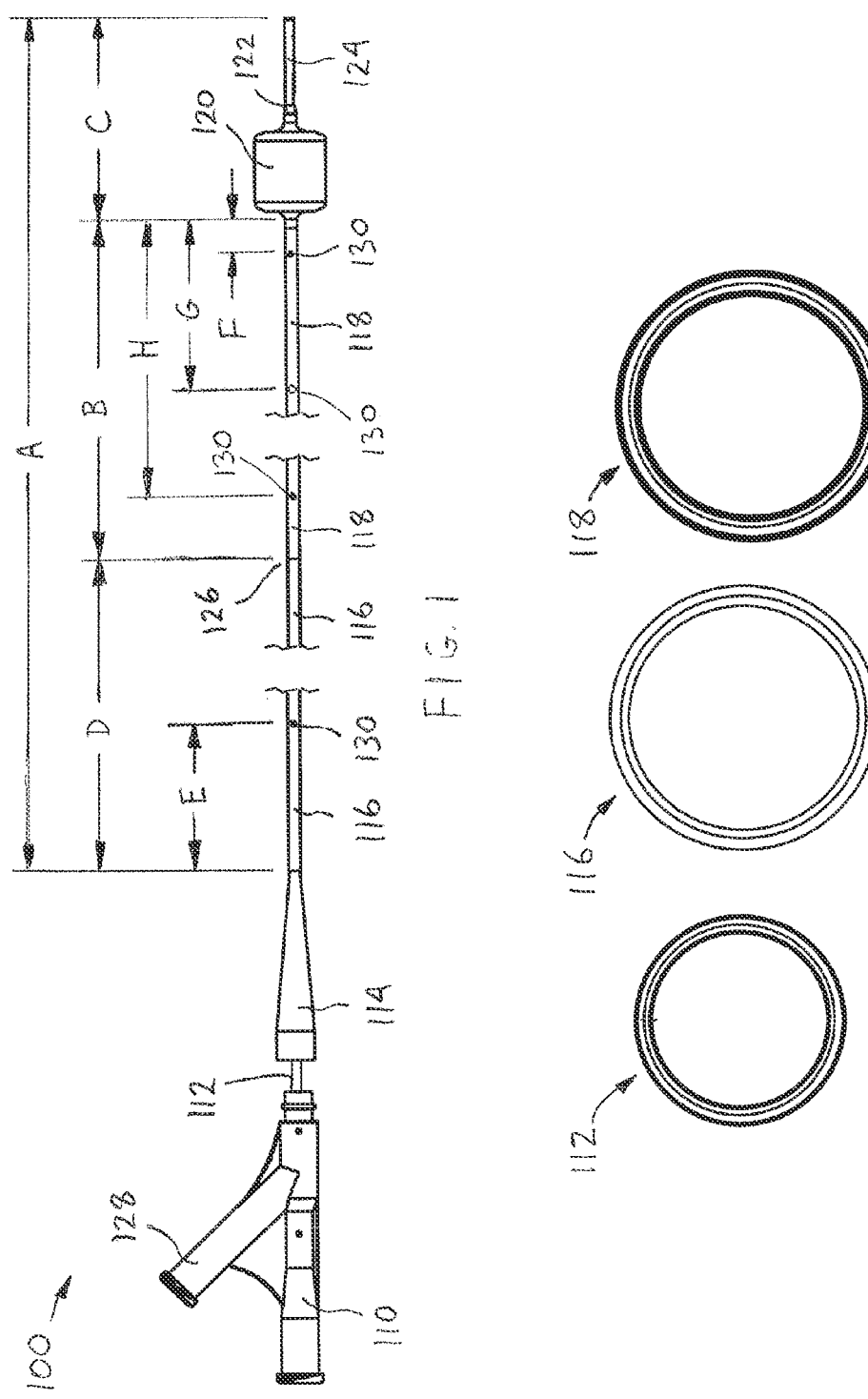

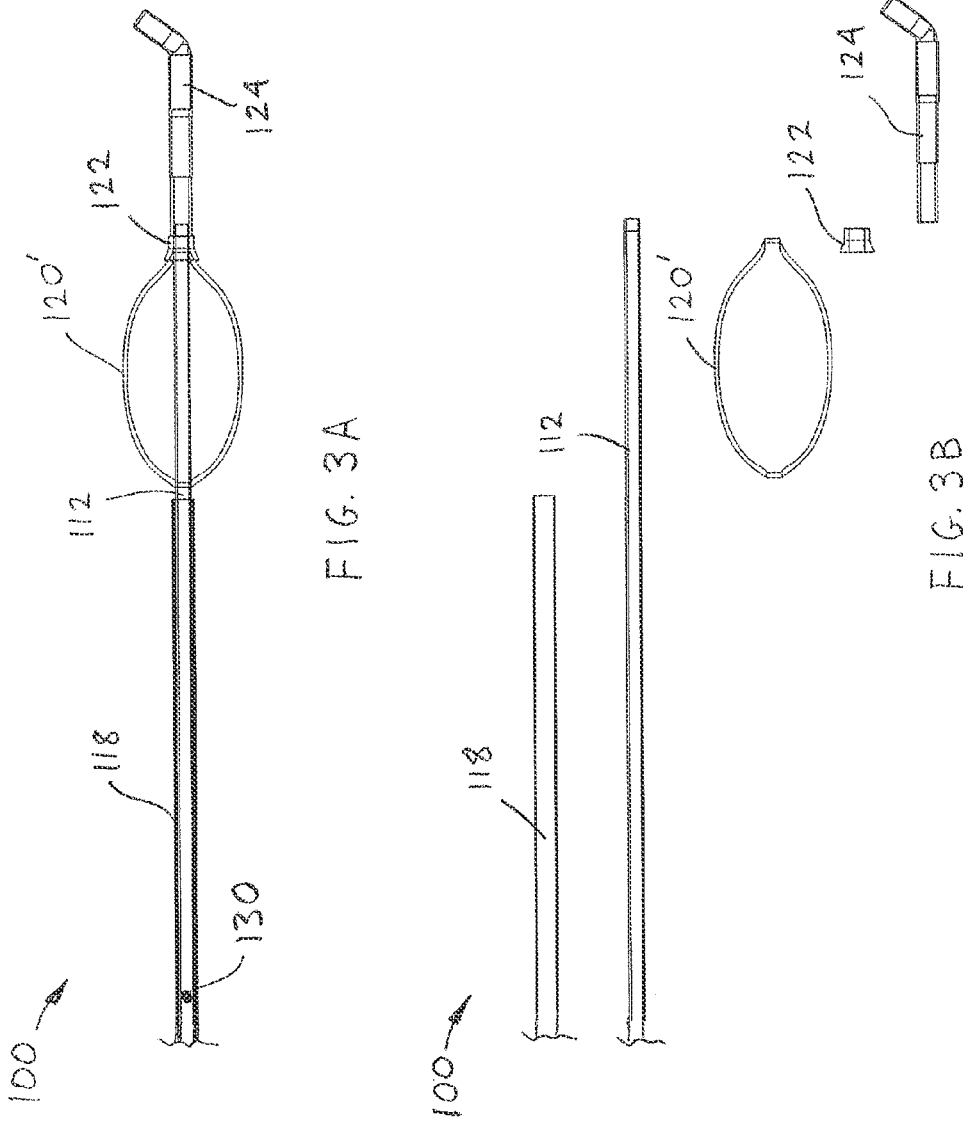

Distal Outer Catheter Section 118

Specimen 1

| Deflection | Test 1 | Test 2 | Test 3 | Avg. |
|---|---|---|---|---|
| 5 mm | 1.8 | 1.5 | 1.6 | 1.6 |
| 10 mm | 2.8 | 3.6 | 3.3 | 3.2 |

Specimen 2

| Deflection | Test 1 | Test 2 | Test 3 | Avg. |
|---|---|---|---|---|
| 5 mm | 2.4 | 2.4 | 2.6 | 2.5 |
| 10 mm | 3.6 | 4.2 | 3.8 | 3.8 |

Specimen 3

| Deflection | Test 1 | Test 2 | Test 3 | Avg. |
|---|---|---|---|---|
| 5 mm | 2.1 | 2.1 | 2.1 | 2.1 |
| 10 mm | 3.4 | 3.3 | 3.2 | 3.3 |

FIG. 7A

Proximal Outer Catheter Section 116

Specimen 1

| Deflection | Test 1 | Test 2 | Test 3 | Avg. |
|---|---|---|---|---|
| 5 mm | 26.1 | 27.37 | 28.46 | 27.3 |
| 10 mm | 38.85 | 42.86 | 42.14 | 41.3 |

Specimen 2

| Deflection | Test 1 | Test 2 | Test 3 | Avg. |
|---|---|---|---|---|
| 5 mm | 27.51 | 18.84 | 18.73 | 21.7 |
| 10 mm | 41.67 | 36.02 | 35.74 | 37.8 |

Specimen 3

| Deflection | Test 1 | Test 2 | Test 3 | Avg. |
|---|---|---|---|---|
| 5 mm | 25.27 | 25.66 | 24.35 | 25.1 |
| 10 mm | 39.98 | 40.12 | 37.71 | 39.3 |

FIG. 7B

Relaxed

10mm Extension

30mm Extension

80mm Extension

BALLOON CATHETERS AND METHODS OF MANUFACTURE AND USE

CROSS REFERENCE TO RELATED APPLICATIONS

This application is a continuation of U.S. application Ser. No. 16/545,519, filed Aug. 20, 2019, now U.S. Pat. No. 11,464,948 (issued Oct. 11, 2022), which is a continuation-in-part application of U.S. application Ser. No. 15/413,262, filed Jan. 23, 2017, now U.S. Pat. No. 10,786,660 (issued Sep. 29, 2020), which is a continuation of U.S. application Ser. No. 15/044,864, filed Feb. 16, 2016, now U.S. Pat. No. 9,550,046 (issued Jan. 24, 2017) which are incorporated by reference herein in their entireties for all purposes.

U.S. application Ser. No. 16/545,519 is also a continuation-in-part application of PCT App. No. PCT/US2019/035966, filed Jun. 7, 2019, which claims priority to U.S. application Ser. No. 16/004,247, filed Jun. 8, 2018, now U.S. Pat. No. 10,350,382 (issued Jul. 16, 2019) which are incorporated by reference herein in their entireties for all purposes.

U.S. application Ser. No. 16/545,519 is also a continuation-in-part application of U.S. application Ser. No. 16/047,922, filed Jul. 27, 2018, which is incorporated by reference herein in its entirety for all purposes.

This application is related to the following patents and applications, which are incorporated by reference herein in their entireties for all purposes: U.S. Pat. Nos. 9,844,383; 9,550,046; and U.S. application Ser. No. 16/047,922, filed Jul. 27, 2018.

INCORPORATION BY REFERENCE

All publications and patent applications mentioned in this specification are herein incorporated by reference for all purposes to the same extent as if each individual publication or patent application was specifically and individually indicated to be incorporated by reference.

BACKGROUND

Catheters are commonly used in medicine for delivery of fluids, therapeutics and implants as well as in sampling tissues and bodily fluids. Catheters can be constructed with balloons or other tools to dilate tissue, block fluid flow or isolate segments of the anatomy. A relatively common use for a catheter is the delivery of drugs to a target tissue using blood vessels as a means of access. When a balloon is used, the vascular compartment distal to the balloon is isolated from the vascular compartment proximal to the balloon and perfusion of diagnostic, therapeutic or embolic agents is localized and concentrated.

One common use for a microcatheter is the delivery of embolic agents and anticancer drugs to a tumor.

According to the NIH, 30,640 people were diagnosed with primary liver cancer (hepatocellular carcinoma, HCC) and 142,820 people were diagnosed with colorectal cancer in the US in 2013. Seventy five percent of these will metastasize to the liver. Liver resection and transplant are the only curative means; however, only small numbers of patients are eligible. Systemic Chemotherapy for primary and metastatic tumors in the liver is ineffective, having a response rate of about 20% and a survival benefit of 10.7 months vs. 7.9 months over symptomatic care.

Trans-Arterial Embolization therapy is the transvascular access for injection of drug and/or embolic agents directly into, or in the vicinity of, the tumor vasculature using a microcatheter. Embolization therapy causes a shutdown of blood flow and, when drug or radioactivity is present, simultaneous release of high concentrations of drug or radioactivity. The technique is also noted for its very low level of toxicity. Chemoembolization was established as a standard of care for intermediate stage hepatocellular carcinoma in 2006. Numerous studies have demonstrated transarterial embolization to be effective on a number of primary cancers and to have better performance than chemotherapy for both HCC and metastatic colorectal cancers in the liver.

Various prior art references provide guidance on aspects of medical catheter construction. For example, U.S. patent application Ser. No. 10/128,977 describes a coaxial catheter whereby a balloon is bonded to an elongated outer tube to prevent the balloon from telescopingly buckling when the balloon is being pushed across a narrow passage. U.S. Pat. No. 6,066,157 describes a coaxial coronary angioplasty catheter whereby an anchor joint is configured to allow distal movement of the inner tube and to prevent proximal movement. U.S. Pat. No. 5,647,198 describes a catheter with a pair of spaced apart balloons that define an intra-balloon space. A lumen passes through the catheter and exits within the intra-balloon space allowing injection of drugs, emulsions, fluids and fluid/solid mixtures. A perfusion lumen or bypass extends from a location proximal to the proximal balloon and to the distal tip to allow shunting of blood past the inflated balloons. U.S. Pat. No. 5,674,198 describes a two balloon catheter that is designed for treating a solid tumor. The balloons are positioned to isolate the blood flow into the tumor and allow injection of a vaso-occlusive collagen material to block the tumor blood supply. Clifton et al. (1963) Cancer 16:444-452 describes a two balloon catheter for the treatment of lung carcinoma. The four lumen catheter includes a lumen for independent injection in the space between the balloons. Rousselot et al. (1965) JAMA 191:707-710 describes a balloon catheter device for delivering anticancer drugs into the liver. See also U.S. Pat. Nos. 6,780,181; 6,835,189; 7,144,407; 7,412,285; 7,481,800; 7,645,259; 7,742,811; U.S. App. No. 2001/008451; U.S. App. No. 2001/0041862; U.S. App. No. 2003/008726; U.S. App. No. 2003/0114878; U.S. App. No. 2005/0267407; U.S. App. No. 2007/0137651; U.S. App. No. 2008/0208118; U.S. App. No. 2009/0182227 and U.S. App. No. 2010/0114021.

An important consideration for transvascular catheters design, especially for use in the peripheral blood circulation, is the desire for the outer diameter ("OD") of the catheter to be as small as possible so that the catheter can access and be advanced into and through small vessels. Another important consideration is that it is generally desirable for a central lumen (e.g., fluid delivery lumen), to be as large as possible to facilitate the delivery of one or more of a therapeutic agent or device therethrough. The wall thickness of one or more catheter shafts of the device influences the size of a central lumen as well as the OD of the device, and thus reducing wall thickness of the shaft(s) can increase in the size of a central lumen as well as reduce the OD of the device.

Some transvascular catheters adapted for use in the peripheral blood circulation include one or more expandable balloons. Because minimizing OD of the device is an important consideration, it is also important that the incorporation of the balloon, including the manner in which it is secured to the device, does not result in an undesirable increase in OD. For example, some previous attempts have bonded balloons to an outer surface of the catheter, which necessarily increases the OD of the catheter (even when unexpanded).

There is thus a continued developmental need for micro-catheters with increased inner lumen size and minimized OD of the device. While the device does not necessarily incorporate an expandable balloon, the size constraints are particularly important when incorporating an expandable balloon.

Additionally, medical catheters may be advanced through torturous vasculature, requiring a flexible distal section that can easily follow the vessel and a stiff proximal section that can support longitudinal advancement of the catheter as it twists and turns through the blood vessels. It is also desirable, in certain applications, that the catheter can transmit torque throughout its length, from the proximal end to a distal region. This is particularly true when a shaped catheter tip is used. Shaped catheter tips may be used to direct a guidewire and/or a catheter around acute angles and into branch vessels. A 90-degree shape is among the favored tip configurations. In use, the catheter tip is rotationally oriented so that the angled tip is pointed toward the desired direction of travel. This requires that proximal catheter rotation translates to distal tip rotation.

In general, flexible catheters may track well through turns in the vasculature but cannot transmit torque well, and stiff catheters can transmit torque but cannot track well though torturous vasculature. Accordingly, there is an unmet medical need for microcatheters that are both trackable and torqueable.

SUMMARY OF THE DISCLOSURE

One aspect of the disclosure is a balloon catheter, comprising: an outer elongate shaft having a wall thickness that is less than 0.0035 inches; an inner elongate shaft with a delivery lumen therein, the inner elongate shaft within the outer elongate shaft having a section that extends distally beyond the outer elongate shaft, the inner elongate shaft having a wall thickness that is less than 0.0035 inches; an adapter secured to a distal region of the outer elongate shaft, the adapter having a distal region extending distally beyond the outer elongate shaft, the distal region of the adapter having an outer surface disposed radially inward relative to an outer surface of a distal end of the outer elongate shaft; an inflatable balloon with a proximal end; a proximal collar radially outside of the proximal end of the balloon, the proximal collar compressing the proximal end of the balloon between the proximal collar and the outer surface of the distal region of the adapter, wherein an inner surface of the proximal end of the balloon is disposed radially inward relative to the outer surface of the distal end of the outer elongate shaft; the inflatable balloon having a distal end stabilized relative to the section of the inner elongate shaft that extends distally beyond the outer elongate shaft, the distal end of the inflatable balloon having an inner surface that is disposed radially inward relative to the outer surface of the distal end of the outer elongate shaft, the outer elongate shaft and the inner elongate shaft forming an inflation lumen that is in communication with the inflatable balloon to allow fluid to be advanced through the inflation lumen and into an internal volume of the balloon to inflate the balloon, wherein the inflatable member is disposed substantially at or below the outer diameter of the outer elongate shaft when in an unexpanded configuration.

The balloon catheter may further include a distal collar radially outside of a distal end of the balloon, the distal collar compressing the distal end of the balloon between the distal collar and the section of the inner elongate shaft that extends distally beyond the outer elongate shaft. The distal collar may be a heat shrink material that compresses the distal end of the balloon. The distal collar may have a thickness from 0.003 mm to 0.05 mm, optionally from 0.006 mm to 0.01 mm. The distal collar may have a length from 0.1 mm to 10 mm, optionally from 0.5 mm to 6 mm. The distal collar may include a polymeric material, and optionally selected from the group consisting of a silicone, latex, polyester, nylon, Pebax, polyethylene, and polyurethane.

The adapter may be secured to an outer surface of the distal region of the outer elongate shaft, and the adaptor may comprise a step from a first region to a second region, the first region extending radially outward further than the second region.

The adapter may be secured to an inner surface of the distal region of the outer elongate shaft. The adapter may include a step from a first region to a second region, the first region extending radially outward further than the second region.

The adapter may have a thickness from 0.0016 mm to 0.025 mm, optionally 0.003 mm to 0.015 mm.

The adapter may have a thickness that is no more than 15% of a wall thickness of the distal end of the outer elongate shaft.

The adapter distal region may have a wall thickness less than 0.01 mm.

The adapter may have a length from 2 mm to 25 mm.

The adapter may include a polymeric material, optionally selected from the group consisting of polyester, nylon, Pebax, polyethylene, and polyurethane.

The proximal collar may include a heat shrink material that compresses the proximal end of the balloon.

The proximal collar may have a thickness from 0.003 mm to 0.05 mm, optionally from 0.006 mm to 0.01 mm.

The proximal collar may have a length from 1 mm to 10 mm, optionally from 1 mm to 6 mm.

The proximal collar may comprise a polymeric material, and optionally selected from the group consisting of a silicone, latex, polyester, nylon, Pebax, polyethylene, and polyurethane.

The balloon may be elastic. The balloon may comprise a silicone material. The balloon may consist essentially of a silicone material.

The balloon catheter may further comprise an adhesive disposed radially between the proximal end of the balloon and the outer surface of the distal region of the adapter.

The balloon catheter may further comprise an adhesive disposed radially between the distal end of the balloon and the section of the inner elongate shaft that extends distally beyond the outer elongate shaft.

The balloon, in an unexpanded configuration, may be disposed at or below the outer diameter of the outer elongate shaft.

The inner surface of the proximal end of the balloon may be at least 0.001 inches below an outer diameter of the outer elongate shaft.

The inner surface of the distal end of the balloon may be at least 0.001 inches below an outer diameter of the outer elongate shaft.

One aspect of the disclosure is a balloon catheter system, comprising: an inner catheter having a lumen extending axially therethrough; an outer catheter outside of the inner catheter; wherein the inner catheter and outer catheter are secured relative to one another at one more discrete connection locations, and the outer catheter including a proximal outer section and a distal outer section, the proximal outer section and the distal outer section meeting at a junction, the distal outer section being more flexible than the proximal outer section; an inflatable member having a distal end that is secured to a section of the inner catheter extending distally beyond the outer catheter, the inflatable member also having a proximal end that is secured relative to the outer catheter; and wherein the outer catheter and the inner catheter form an inflation lumen therebetween in fluid communication with an interior of the inflatable member to allow an inflation fluid to be advanced through the inflation lumen to inflate the inflatable member.

The one or more discrete connection locations can include a first discrete connection location at which the inner catheter is connected to the proximal outer section, and a second discrete connection location at which the inner catheter is connected to the distal outer section. The inner catheter may be connected to the outer catheter at the first and second discrete connection locations with an adhesive.

The catheter system may further comprise a distal tip section extending distally beyond the inflatable member, the distal tip having a preset shape extending laterally outward relative to a longitudinal axis.

The proximal outer section may extend distally from a strain relief section to the distal outer section. The distal outer section may extend from the junction to the adaptor.

The distal outer section may have a length that is at least 20 cm.

The proximal outer section may have a length of about 20 cm.

The inner catheter may include a braided material extending along its length.

The distal outer section may have a length that is at least 20 cm.

The outer catheter may include a braided material extending along its length.

BRIEF DESCRIPTION OF THE DRAWINGS

FIG. 1 is a fragmentary side view showing an exemplary vascular catheter system.

FIG. 2 is a cross-sectional view showing lateral cross-sections of an exemplary inner catheter, proximal outer catheter section, and distal outer catheter section.

FIG. 3A is a side view showing the distal portion of an exemplary catheter system.

FIG. 3B is an exploded side view of the distal portion shown in FIG. 3A.

FIG. 7A is a chart showing results (in grams) from flexibility testing performed on three sample specimens of an exemplary distal outer catheter section.

FIG. 7B is a chart showing results (in grams) from flexibility testing performed on three sample specimens of an exemplary proximal outer catheter section.

DETAILED DESCRIPTION

Figures 4, 5A, 5B, 5C, 5D:
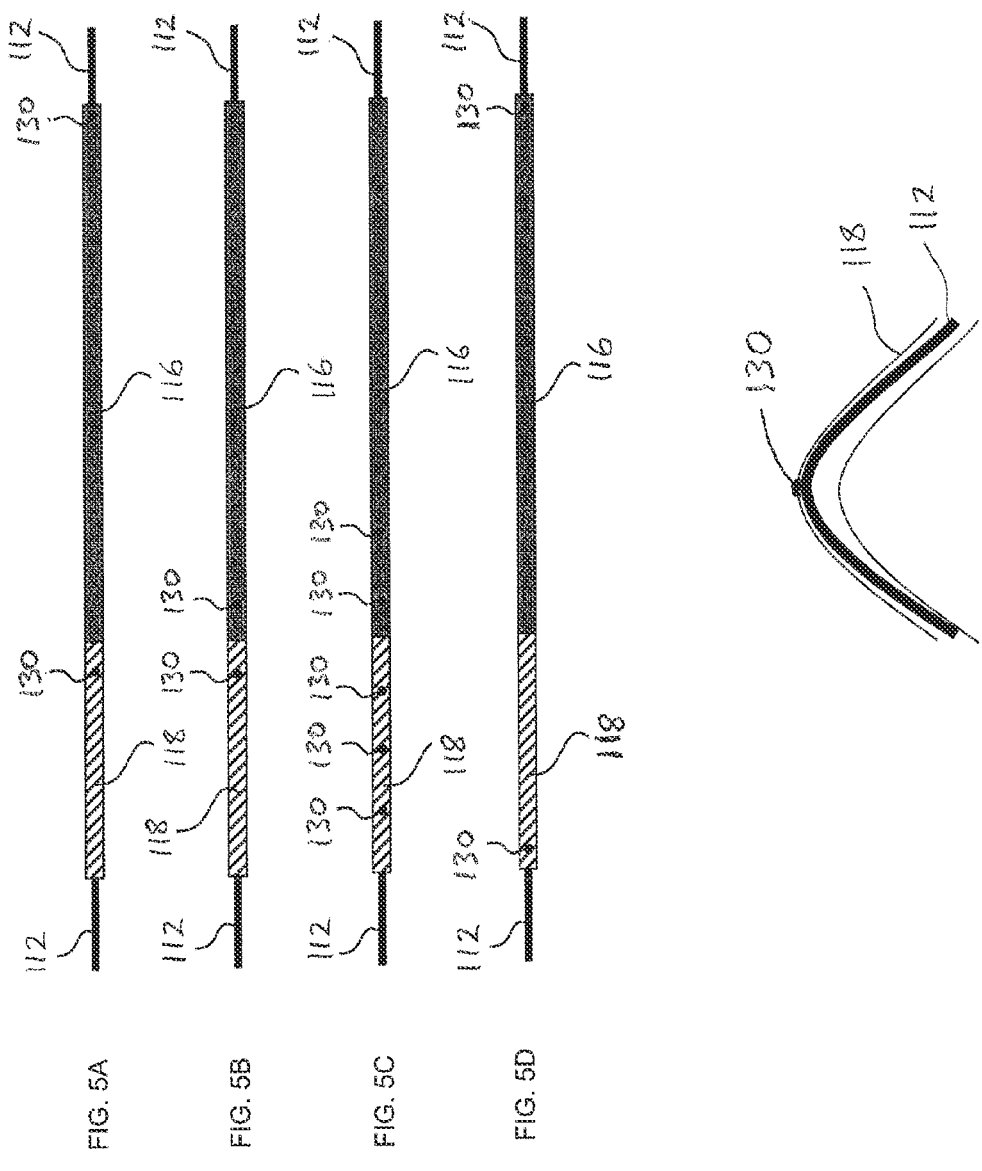
FIG. 4 is a side cross-sectional view showing a bend in a distal outer catheter section and an inner catheter.
FIGS. 5A-5D are side views showing various exemplary catheters with inner and outer catheters.

This disclosure relates generally to catheters, their methods of use, and manufacture. The embodiments herein may be particularly suited for microcatheters that are adapted and configured to be advanced through small vessels. The embodiments herein may be particularly suited for microcatheters that are adapted and configured to deliver a therapeutic agent (e.g., fluid or device) through a delivery lumen. It is understand that the embodiments herein are illustrative, and that not every feature described with respect to any particular embodiment is required or limiting. For example, while some of the embodiments herein include one or more expandable balloons, it is understand that a balloon need not necessarily be incorporated into any particular embodiment herein, and that inventive concepts herein need not necessarily include a balloon. Additionally, for example, while some of the embodiments herein may include outer and inner catheters that are secured together at discrete connection locations, it is understood that discrete connection locations need not necessarily be incorporated into any particular embodiment, and that inventive concepts herein do not necessarily include discrete connection locations.

Some embodiments herein describe microcatheters that include an outer catheter (which may be referred to as an outer shaft) and an inner catheter (which may be referred to as an inner shaft), where a portion of the inner catheter extends distally beyond the outer catheter. An expandable balloon may be secured relative to a distal end of the outer catheter and relative to the portion of the inner catheter extending distally beyond the outer catheter, to thereby create fluid-tight couplings that allow fluid to be advanced through a lumen created between the inner and outer catheters and into the balloon to expand the balloon.

Advantageously, the outer and inner catheters are thin-walled, providing the advantage of increasing the size of a delivery lumen within the inner catheter while minimizing the outer diameter ("OD") of the overall device. In any of the embodiments herein, the outer catheter wall and/or the inner catheter wall may have a thickness from 0.0005" to 0.005".

Some of the embodiments herein include one or more expandable balloons. Advantageously, the surfaces of the balloon that are secured to the device (e.g., a radially inner surface of a proximal end of the balloon, and a radially inner surface of the distal end of the balloon) are disposed radially inward relative to the OD of the outer catheter. Bonding the balloon in this manner helps maintain the balloon, when unexpanded, at or below the OD of the outer catheter, which helps minimize the OD of the system, the advantages of which are described herein.

While not necessarily required, there may be one or more aspects of the balloon bonding(s) regions of the device that help minimize the OD of the device. For example, without limitation, one or more of any collars (which may be referred to herein as sheaths) or adaptors herein that might be incorporated into the device may have one or more dimensions (e.g., thickness, length) that are sized to help minimize the OD of the device.

Some embodiments herein include a shaft region with a proximal section that is stiffer than a distal section. The stiffer proximal section is adapted to translate torque to the more flexible distal section, while the more flexible distal region allows the device to be tracked through small vessels.

Additionally, while not necessarily required, some embodiments herein include outer and inner catheters that are secured together at discrete connection locations. At the discrete connection locations, movement between an inner surface of the outer catheter and an outer surface of the inner catheter is resisted.

A standard microcatheter for drug delivery is designed to access small vasculature and necessarily has a small outer diameter in the range of 0.5 mm to 2 mm more optimally 0.75 mm to 1 mm. For use in the peripheral vasculature, and in particular for tumor embolization, delivery catheters are typically 50 cm to 210 cm in length. Once the catheter is oriented at a target site within the blood vessel, drug, embolic agents, contrast or other fluids are injected through a lumen that extends longitudinally from proximal to distal ends. It is common that the fluids are viscous and must be injected at high flow rates in the range of 1 ml/second to 10 ml/second. However, flow rate is limited by injection lumen diameter or cross sectional area, length and the ability of the catheter wall to withstand high pressures in the range of 250 psi to 2000 psi, more typically in the range of 500 psi to 1,500 psi. Given that the catheter length is fixed by the requirements of the transvascular procedure, flow rate can be maximized by making the injection lumen and injection pressure tolerance as high as possible.

When considering a balloon microcatheter, an additional lumen that extends longitudinally from proximal to distal ends of the catheter is added for balloon inflation and deflation. In many embodiments, it is optimal for the balloon to inflate and deflate in as short a time as possible and in the range or 10 seconds to a maximum of 60 seconds. When balloons occlude or dilate blood vessels, it can be necessary for deflation to occur rapidly to avoid complications. Often the balloon is inflated with radiopaque contrast which is a viscous fluid. Therefore, it is desirable that the balloon inflation lumen also be as large as possible.

Since microcatheters have small cross sections, it is a challenge to achieve both rapid drug injection speed, which favors large central injection lumen size, and rapid balloon inflation and deflation times, which favor large balloon inflation lumens.

Further, it would be highly desirable for a mounted balloon not to increase the outer diameter of the catheter since it preferably maintains a small profile and it is optimal to mount the balloon so that in its retracted configuration it does not extend beyond the outer diameter of the catheter.

FIGS. 1 and 2 illustrate an exemplary embodiment of a catheter system. It is understood that the embodiment is illustrative and not limited by all aspects included therein. One or more features may be optional.

FIGS. 1 and 2 illustrate an exemplary coaxial catheter designs that allows torque to be effectively transmitted from a relatively stiff catheter section to a relatively flexible catheter section. The catheter includes an outer catheter having at least two sections, including at least one high torque stiff section and one low torque flexible section. In this embodiment, the outer catheter is mechanically connected to the inner catheter in at least one discrete connection point on the stiffer proximal section and at least one discrete connection point on the more flexible distal section.

As shown in FIG. 1, an exemplary high torque vascular catheter system 100 constructed according to aspects of the present disclosure includes a Y-hub 110, an inner catheter 112, a strain relief 114, a proximal outer catheter section 116, a distal outer catheter section 118, an inflatable balloon 120, a marker band 122, and a distal tip segment 124. Y-hub 110 is shown separated from strain relief 114 for clarity in FIG. 1, but normally is connected thereto. Proximal outer catheter section 116 extends from inside Y-hub 110 to a junction point 126 with distal outer catheter section 118. Distal outer catheter section 118 extends from junction point 126 towards the proximal end of balloon 120, and the proximal end of balloon 120 is fluidically sealed relative to the distal end of the distal outer catheter section 118. Proximal outer catheter section 116 may be joined to distal outer catheter section 118 with a butt joint weld at junction point 126 such that the outer catheter is fluid pressure tight. The proximal and distal outer catheter sections may be joined using other joint types, such as with the proximal or distal section overlapping (radially outside of) the other, such as with a step configuration or tapering configuration.

Inner catheter 112 extends from within Y-hub 110, through proximal outer catheter section 116, distal outer catheter section 118, balloon 120, optional marker band 122, and into the proximal end of distal tip segment 124. In this exemplary embodiment, the distal end of balloon 120 is fluidically sealed near the distal end of inner catheter 112. With this arrangement, a first generally annular volume (not shown) is created between an outer diameter of the inner catheter 112 and an inner diameter of the proximal outer catheter section 116. This volume may also be referred to herein as fluid pathway, or fluid lumen. Similarly, a second generally annular volume (not shown) remains between the outer diameter of the inner catheter 112 and an inner diameter of the distal outer catheter section 118. These first and second generally annular volumes are in fluid communication with one another at junction point 126. In some embodiments, inner catheter 112 may be generally free to move laterally inside proximal outer catheter section 116 and distal outer catheter section 118. As such, inner catheter 112 may contact these outer catheter sections (as depicted in FIG. 4), and the generally annular volumes may become crescent shaped. What is meant by "generally annular volume" in this context is the space between inner catheter 112 and outer catheter sections 116 and 118, regardless of whether it always has an annular shape.

The first annular volume described above is in fluid communication inside Y-hub 110 with its lateral port 128. The second annular volume is in fluid communication with the interior of balloon 120. Accordingly, when a balloon inflation pressure is provided at lateral port 128, balloon 120 inflates as shown in FIG. 1. When the inflation pressure is removed from lateral port 128, balloon 120 deflates and returns to a retracted state (not shown) surrounding the distal region of inner catheter 112.

In some embodiments, catheter system 100 may have a working length A (i.e. outside of Y-hub 110 and strain relief 114) of about 50 cm to about 210 cm. In some embodiments, the length B of distal outer catheter section 118 is about 20 cm-40 cm, such as about 25 cm-35 cm, such as about 30 cm. In some embodiments, the diameter of balloon 120 is about 2 mm-10 mm, such as 4 mm-8 mm such as about 6 mm, its length is about 5 mm-15 mm, such as about 10 mm, and the length of distal tip segment 124 is about 5 mm-12 mm, such as about 8 mm. A combined distance C of balloon and tip may be about 1 cm-2.7 cm, such as about 2 cm, and a total distance B+C distal to junction point 126 may be about 21 cm-42.7 cm, such as about 32 cm. Length D may be about 70 cm-130 cm, such as about 119 cm (the portion of proximal outer catheter section 116 that extends from Y-hub 110 and strain relief 114). In some implementations, catheter system 100 is introduced into the target vasculature through a diagnostic catheter (not shown.) In some of these implementations, depending on the application, it may be desirable to have about 30-32 cm of flexible catheter section (e.g. B+C) extending from the diagnostic catheter in order to track through tortuous vasculature. Therefore, with the aforementioned dimensions, junction point 126 and the distal portion of proximal outer catheter section 116 remain inside the diagnostic catheter during a medical procedure. Depending on the vascular pathway that is used to advance the balloon towards the target anatomical location, it may be possible to vary the length D for any particular device, while keeping the length B+C the same. For example without limitations, a femoral artery access location may be used in some procedures, while in some procedures a radial artery access may be used. Length D may vary for each of the different procedures, but the length B+C could be the same.

Referring to FIG. 2, cross-sections of inner catheter 112, proximal outer catheter section 116, and distal outer catheter section 118 are shown. In this exemplary embodiment, each of these three components comprises an inner layer, a middle layer and an outer layer. In some implementations, a guidewire is advanced through the inner lumen of catheter system 100. In such instances it is therefore desirable that the inner layer of the inner catheter be lubricious. Materials that can be used include, but are not limited to, fluoropolymers PTFE, FEP, PFA, EFEP, and HDPE. It is often the case that viscous contrast materials are injected through the inner lumen of the inner catheter, requiring that it withstand high pressures. Support materials that are commonly used include metals such as stainless steel or nitinol that are braided or coiled.

The materials that can be used for the outer layer of the inner catheter need not be a thermoplastic and are selected to provide strength, dimensional stability and flexibility, including, but not limited to, HDPE, Nylon, Polyimide, Polyester, PEBAX and TECOFLEX.

Transvascular catheters require pushability to advance through torturous vessels and to be twisted or torqued. The proximal outer catheter section is constructed to have pushability and torqueability. Therefore, stiffer materials with higher durometers can be used such as HDPE, Nylon, Polyimide, Epoxy, Polyester, PEBAX, TECOFLEX and fluoropolymers. The distal outer catheter will be advanced into small torturous vessels and must be flexible. In this instance, lower durometers of the materials mentioned above can be used.

Referring to FIGS. 3A and 3B, enlarged views showing an exemplary distal portion of catheter system 100 are provided. FIG. 3A shows an assembled view of the distal portion, and FIG. 3B shows an exploded view. Inflated balloon 120' shown in FIGS. 3A and 3B has a more rounded profile than that of balloon 120 shown in FIG. 1. As best seen in FIG. 3A, distal outer catheter section 118 stops just short of the proximal end of balloon 120'. To seal the proximal end of balloon 120' against the distal end of distal outer catheter section 118, a stepped inner sleeve and/or an outer sleeve (neither shown) may be utilized.

Any of the balloons and balloon bonding concepts described elsewhere herein may be incorporated or used in place of the balloon and/or balloon bonding described in reference to system 100.

As shown in FIGS. 3A and 3B, distal tip segment 124 may optionally be provided with a preset shape that extends a distal end thereof laterally outward. In this embodiment, the distal end extends outward at a 45 degree angle. In other embodiments (not shown), the distal end extends outward at an angle of about 70 to about 90 degrees. In still other embodiments, the tip angle can be between about 10 degrees and about 70 degrees, or between about 90 degrees and about 180 degrees (i.e. the tip can double back on itself.) In some embodiments (not shown), the tip can include two or more bends rather than the single bend of the exemplary embodiment shown. This outward angle allows a medical practitioner to rotate the distal tip segment 124 towards a branch blood vessel (by rotating Y-hub 110 outside of the patient), extend a guidewire (not shown) distally from the distal tip segment 124 into the branch blood vessel, and then track the catheter system 100 over the guidewire into the branch blood vessel. This may be done repeatedly to track the catheter system 100 deep into tortuous vasculature toward target tissue.

As depicted in FIG. 3A, distal outer catheter section 118 may be connected to inner catheter 112 through at least one discrete connection point 130, which can help transfer torque between the inner and outer catheters. In some embodiments, discrete connection point(s) 130 may be created by thermal or chemical bonding. For example, laser, radio frequency energy and/or a heated probe such as a soldering iron may be used to melt together the materials of distal outer catheter section 118 and inner catheter 112 to form a tack or spot weld. By way of another example, a hole may be formed in distal outer catheter section 118 and a small amount of glue, adhesive, epoxy or other fluid material may be injected into the hole to bond the two catheters 118 and 112 together. In some embodiments, the resulting discrete connection point 130 described above may have a diameter no greater than 0.006 inches. In some embodiments, the resulting discrete connection point 130 may extend through a circumferential angle no greater than about 30 degrees. In other embodiments (not shown), through pins, wires, micro-rivets, etc. may be used to create the discrete connection points.

As depicted in FIG. 4, when creating a discrete connection point 130, in some embodiments it may be desirable to bend distal outer catheter section 118 and inner catheter 112 so that they make contact with one another. With this approach, a nominal gap of 0.003 inches between inner catheter 112 and distal outer catheter section 118 becomes 0.000 inches on the outside of the bend and 0.006 on the inside of the bend. If a glue or other fluid material is being used to create the discrete connection point 130, the fluid may wick further in the axial direction than in the circumferential direction, creating an oblong discrete connection point 130. In some embodiments, a hole in distal outer catheter section 118 through which the fluid is injected may be no larger than about 0.006. Similar discrete connection points 130 may also be formed between proximal outer catheter 116 and inner catheter 112. The creation of discrete connection points 130 should maintain the patency of the balloon inflation passage between the inner and outer catheters. That is, the connection points cannot be such that they completely block the flow of inflation fluid to the balloon, or else the balloon could not be inflated.

Referring to FIGS. 5A-5D, various exemplary catheters constructed according to aspects of the present disclosure are depicted. In these views, the proximal end of the catheter is shown on the right, the distal end is shown on the left, and other components such as a Y-hub, strain relief, balloon, marker band, and distal tip segment (which may or may not be present) are removed for clarity. A sufficient number and placement of discrete connection points 130 should be created to ensure that torque can be adequately transferred from proximal outer catheter 116 to distal outer catheter section 118 through inner catheter 112. However, the number of discrete connection points should be kept to a minimum and their locations chosen so that good flexibility of the catheter is maintained. Each of the exemplary constructs shown in FIGS. 5A-5D is believed to achieve both these goals, as well as other possible constructs. All of the discrete connection points shown in FIGS. 5A-5D are shown on the near side of the catheter for clarity, but in some embodiments they are placed on alternating sides or spaced around the circumference of the catheter so that the catheter is not significantly stiffer along one or two sides.

Referring again to FIG. 1, another exemplary layout of discrete connection points 130 is shown. In this exemplary embodiment, there is one discrete connection point 130 formed between proximal outer catheter 116 and inner catheter 112, and three discrete connection points 130 formed between distal outer catheter section 118 and inner catheter 112. Y-hub 110 may also serve to connect proximal outer catheter 116 and inner catheter 112. The discrete connection point 130 formed between proximal outer catheter 116 and inner catheter 112 may be a distance E away from strain relief 114 as shown, which in some embodiments is between about 2 cm and about 10 cm. The three discrete connection points 130 formed between distal outer catheter section 118 and inner catheter 112 may be predetermined distances F, G and H, respectively, away from the proximal end of balloon 120 as shown. In some embodiments, these distances are about 1 cm-3 cm, such as 2 cm, about 5 cm-15 cm, such as about 10 cm, and about 20 cm-30 cm, such as about 25 cm, respectively. The middle of these three discrete connection points 130 may be located on the opposite side from the other two, that is, 180 degrees away around the circumference.

Figure 6:
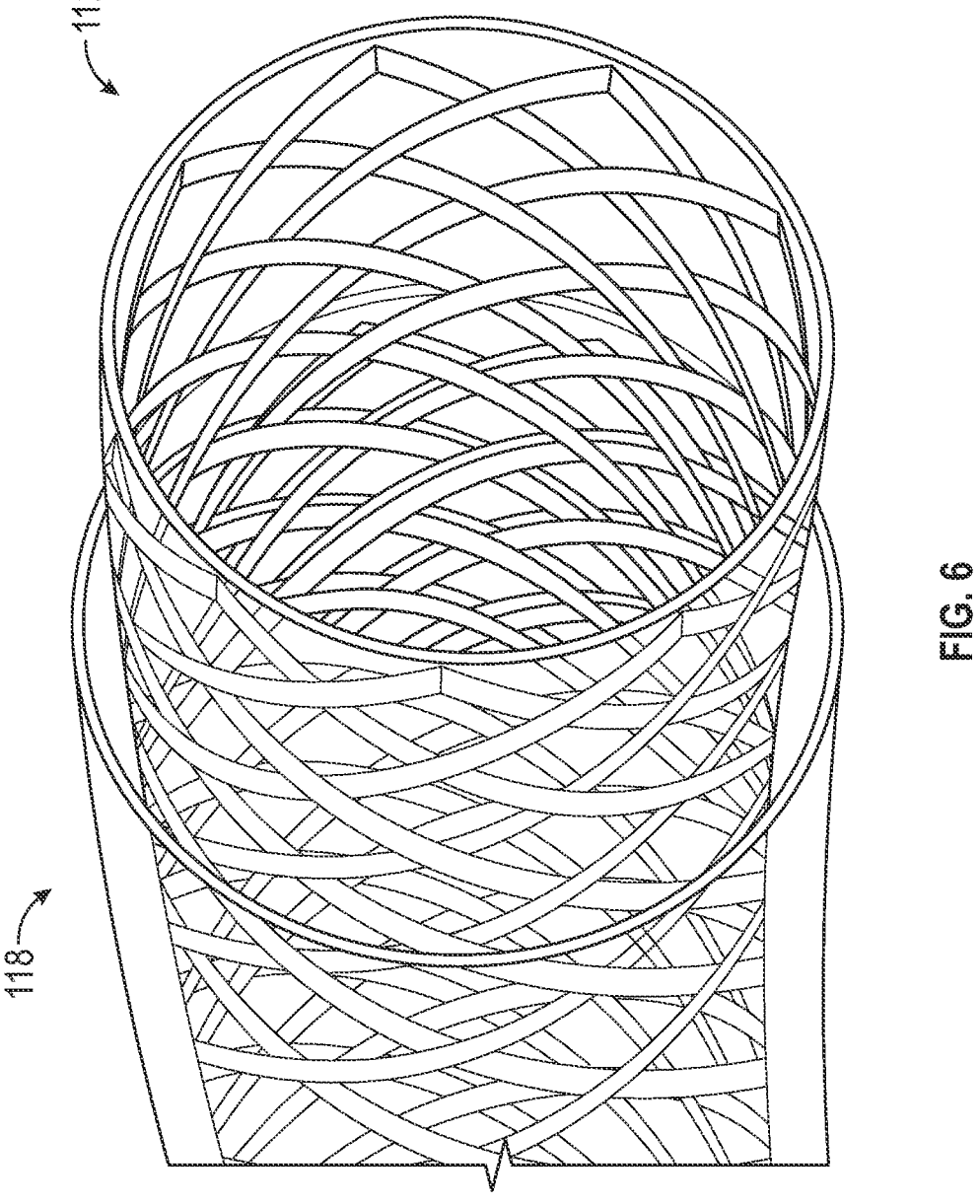
FIG. 6 is an enlarged perspective view showing an inner catheter located inside an outer catheter section in an exemplary embodiment.

Referring to FIG. 6, an enlarged view showing inner catheter 112 located inside distal outer catheter section 118 is provided. As can be seen, in this exemplary embodiment both inner catheter 122 and distal outer catheter section 118 have internal mesh or braid structures.

In order to be able to track through tortuous vasculature, the distal portion of system 100 should be very flexible. However, very flexible portions of a catheter system tend to transmit torque poorly, as previously mentioned. If a catheter system does not have sufficient torsional rigidity, there is a delay or hysteresis between rotations that are input at the proximal end of the catheter and the desired output rotations that occur at the distal end. In some cases of poor torsional rigidity in the prior art, the proximal end of the catheter may be turned 2, 3 or more rotations for every 1 rotation that occurs at the distal end, with the additional rotations being stored as potential energy in the catheter. These additional rotations may or may not be eventually released, and may release suddenly and unexpectedly. In some implementations of tracking through tortuous vasculature, the proximal end of a prior art catheter may be turned 10 or more times with no rotation occurring at the distal end. With the unique combination of materials, dimensions and discrete connection points 130 disclosed herein, Applicants have found that catheter systems may be constructed that are both highly trackable and torqueable.

Referring to FIGS. 7A and 7B, results from flexibility testing performed on three sample specimens of an exemplary distal outer catheter section 118 (FIG. 7A) and three sample specimens of an exemplary proximal outer catheter section 116 (FIG. 7B) are provided (in grams.) For each of the tests, a 3-point load fixture was used, with one side of the specimen pinned, the other side 5 cm away and resting on the fixture (to alleviate slack), and a force transducer placed in the center of the 5 cm span. The center of each catheter specimen was deflected either 5 mm or 10 mm and a reading from the transducer was recorded (in grams.) Each specimen was tested three times and the results were averaged as shown.

As can be seen by the test results, the distal outer catheter section 118 (FIG. 7A) is significantly more flexible than the proximal outer catheter section 116. In this exemplary embodiment and test set up, the proximal outer catheter sections 116 generally exhibit readings of about 1000% of those for the distal outer catheter sections 118. In other embodiments, the proximal outer catheter sections 116 may generally exhibit readings of about 150%, 200%, 500%, 800% or more compared to those for the distal outer catheter sections 118. Other testing methods may also be used to compare the flexibility of the proximal and distal outer catheter sections.

In some embodiments in this disclosure, the catheter system also includes one or more expandable balloons. As mentioned elsewhere, previous attempts at securing a balloon to a catheter secured one or more balloon surfaces to an OD of the catheter, which necessarily increases the OD of the system. In embodiments herein that include a balloon, an inner balloon bonding/securing surface is advantageously disposed radially inward relative to an outer diameter (outer surface) of an outer catheter, which allows for the OD of system to be minimized. In embodiments herein that include a balloon, the balloon is secured to the device such that substantially all, if not all, of the balloon is disposed at or below the OD of the outer catheter. In some embodiments, a balloon is positioned below the surface of the catheter when in its constrained configuration and returns thereto following inflation and deflation. Some embodiments herein include a circumferentially oriented pocket or pockets in a catheter and one or more balloon bonding surfaces are positioned below the surface of the catheter.

When this disclosure refers to a balloon bonding surface, it refers to a balloon surface that is secured relative to another surface. It does not require that the balloon be secured to the other surface in a particular manner. For example, a bonding surface does not require that the balloon surface be secured to the other surface with an adhesive.

In any of the embodiments herein, the balloon surface that is bound to another surface may be at least 0.001 inches or more below the outer diameter (outer surface) of the outer catheter, as long as the fluid passageway remains between the inner and outer catheters for the fluid to be advanced.

As set forth herein, transvascular microcatheters should include a distal region that is flexible. In embodiments that includes a distal balloon (such as some of those herein), the catheter must also be flexible at the location of the balloon that is mounted at the distal portion of the catheter to allow them to advance through tortuous vasculature. Balloon bonding adhesives, if used, tend to be rigid and measures should be taken to construct the balloon bonding surfaces to be flexible.

Therefore, in many embodiments, optimal characteristics of a balloon microcatheter include: 1) a large drug injection lumen, 2) a large balloon inflation lumen, 3) a catheter that withstands high pressure, 4) a rigid proximal section that is pushable and torqueable, 5) a flexible distal catheter portion; and 6) a small outer diameter. The different embodiments herein provide for one or more of these advantages.

Strong bonding of the balloon to the catheter is also important to prevent detachment during a medical procedure and to assure that post inflation, the balloon can return to a position at or below the surface of the outer diameter of the catheter.

Many of the methods and devices herein solve the aforementioned challenges and enable a balloon microcatheter to be adapted to include a large injection lumen, a large balloon inflation lumen, a flexible distal catheter portion and strong balloon bonding that assure the balloon will return to a retracted diameter less than or equal to that of the catheter's outer diameter.

The devices of the present disclosure include a balloon that is secured to a catheter such that the balloon bonds are positioned below the outer surface (i.e. radially inward of the outside diameter) of the catheter assembly and, if desired, the balloon in its uninflated configuration can be positioned below or at the outer surface of the catheter assembly. The present device allows a balloon to be inflated from below the surface of a catheter assembly and when deflated, return thereto. Such a balloon catheter assembly, as disclosed herein, has a small profile, a strong attachment of the balloon to the catheter and rapid inflation and deflation times even with viscous solutions.

Any of the balloon and/or balloon bonding embodiments herein may be integrated or used with any of the other aspects of any catheter herein. For example, any of the balloon and/or balloon concepts herein can be used with any of the embodiments illustrating exemplary inner and outer catheters (e.g., FIGS. 1-6)

Figures 8, 9:
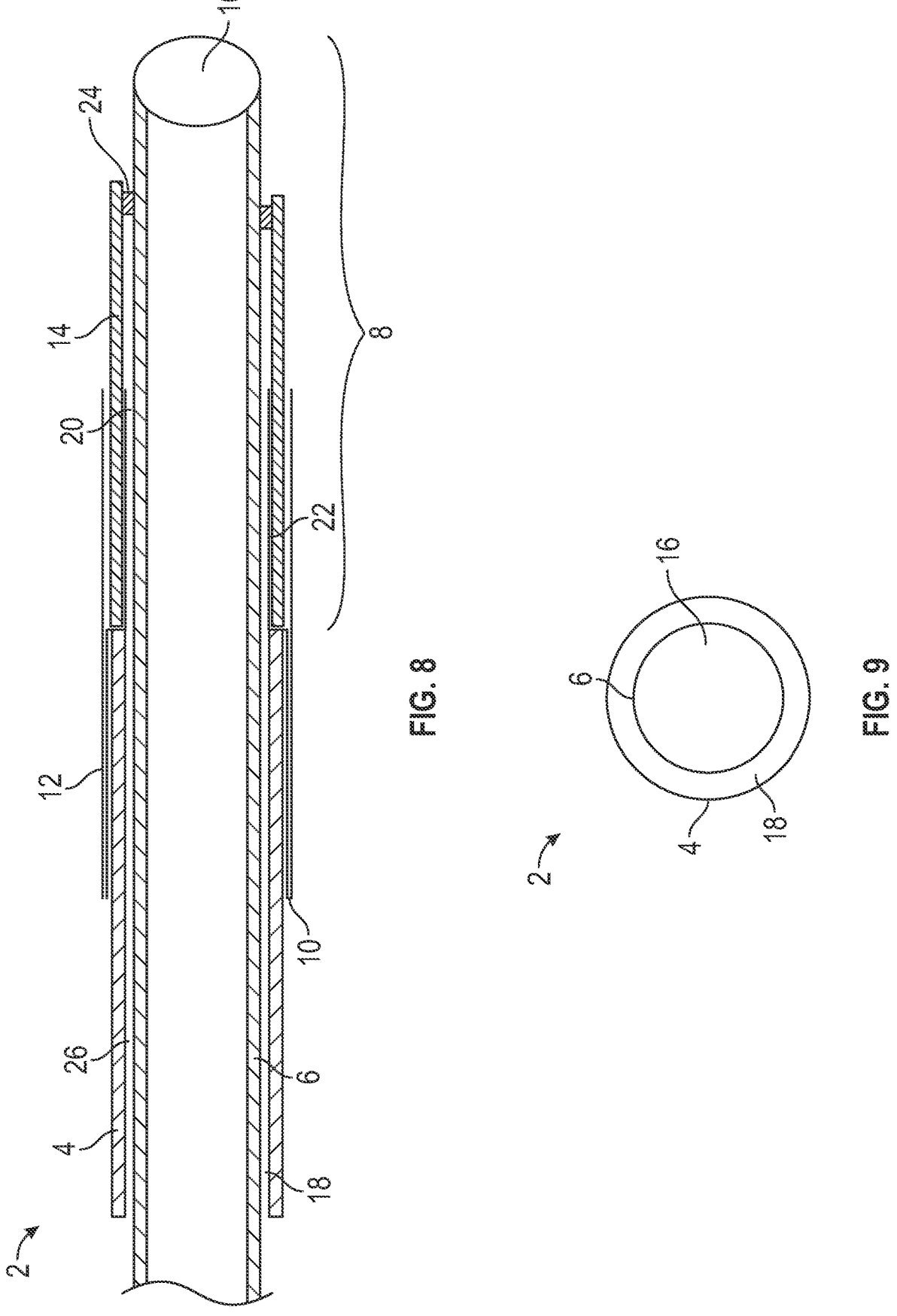
FIG. 8 is a longitudinal cross section of an exemplary embodiment in which balloon bonds are below an outer surface of an outer catheter.
FIG. 9 is an axial cross section of a coaxial catheter.

Referring to FIG. 8, a longitudinal cross section of the distal end of an exemplary embodiment of the present disclosure is shown with catheter assembly 2, outer catheter 4, inner catheter 6, inner catheter extension 8, optional outer adapter 10, support sheath 12, balloon 14, inner catheter lumen 16, annular lumen 18, fluid channel 20, proximal balloon bond 22, and distal balloon bond 24. In this embodiment, a coaxial catheter design is shown with outer catheter 4, having a proximal end and a distal end and a diameter larger than inner catheter 6, also having a proximal end and a distal end, whereby inner catheter 6 is positioned longitudinally inside of outer catheter 4. Inner catheter 6 extends distally beyond the distal end of outer catheter 4, as indicated by extension distance 8, said inner catheter extension providing a reduction in diameter whereupon a balloon or accessory can be attached. The inner and outer catheter may be any of the inner and outer catheters herein, including any of the optional discrete connection locations between the inner and outer catheters.

Inner catheter 6 and outer catheter 4 may be composed of a laminate or composite of at least two layers, with a steel or other braid, coil, woven, and/or reinforcing material positioned between the layers or forming one of the layers. In some embodiments, a reinforcing material is molded within a less rigid base material such that the reinforcing layer is embedded in an encapsulation layer. This construction is provided to allow kink resistance and strength to withstand high pressure injection. Given the multi-layer construction, these walls typically have a thickness of 0.1 mm to 1 mm which consumes radial area which could otherwise be used to increase the size of the injection lumen or balloon inflation lumen. Therefore, thin wall construction is optimal, provided that strength, kink resistance and a tolerance to high pressure is maintained. In this exemplary embodiment, outer adapter 10 is composed of a single layer flexible material such as Pebax, polyamide, PET, polyethylene, polyurethane or the like and has a wall thickness of 0.0016 mm to 0.025 mm, more typically 0.003 mm to 0.0150 mm, said thickness being less than that of the inner catheter or outer catheter. In some embodiments, the outer catheter 4 has a wall thickness of about 0.0635 mm and the outer adapter 10 has a wall thickness of about 0.00635 mm. In some embodiments, the wall thickness of the outer adapter 10 is no more than about 15% of the wall thickness of the outer catheter 4. The thickness and material type is different from that of the outer catheter and optimized for maximizing balloon inflation and injection lumen diameters, flexibility and bondability of the balloon material to the adapter.

In any of the embodiments herein, the wall thickness of the inner catheter is from 0.0001 inches to 0.0040 inches, such as from 0.001 inches to 0.0035 inches, such as 0.0015 inches to 0.003 inches. In any of the embodiments herein, the wall thickness of the outer catheter is from 0.0001 inches to 0.0040 inches, such as from 0.001 inches to 0.0035 inches, such as 0.0015 inches to 0.003 inches. The inner and outer catheters can include any number of "layers," such as any of the three-layered constructs described herein.

In some embodiments, the proximal end of outer adapter 10 is circumferentially oriented about the outer surface of the distal end of outer catheter 4 and steps centrally to a reduced diameter at a point distal to the distal end of outer catheter 4, said reduced diameter is circumferentially oriented about inner catheter 6. At its proximal end, support sheath 12 is positioned over the distal end of outer catheter 4 and the proximal end of outer adapter 10, and the distal end of support sheath 12 is positioned over the proximal end of balloon 14. Support sheath 12 can compress the proximal end of balloon 14 into the space below the other diameter of outer catheter 4, assuring that the balloon will return to a position at or below the outer diameter of outer catheter 4 and strengthens balloon bond 22 on outer adapter 10. In some exemplary embodiments, any support sheath herein is composed of a single layer flexible material with substantially the same wall thickness and material composition as an adapter, such as an outer adaptor.

The proximal end of inner catheter 6 is in fluid communication with the distal end of inner catheter 6 by way of inner catheter lumen 16. A space between outer catheter 4 and inner catheter 6 defines a generally annular lumen 18, and a space between the reduced diameter of outer adapter 10 and inner catheter 6 defines fluid channel 20. Balloon 14 is bonded at its proximal end to the reduced diameter of outside adapter 10 by proximal balloon bond 22, and the distal end of balloon 14 is bonded to inside catheter 6 at distal balloon bond 24, such that proximal balloon bond 22 and distal balloon bond 24 are radially inward from the outside diameter of outer catheter 4. In this exemplary embodiment, proximal balloon bond 22 and distal balloon bond 24 are also radially inward from the inside diameter of outer catheter 4, as shown in FIG. 1. Radially inner surfaces of the balloon at the proximal and distal ends of the balloon are disposed radially inward relative to the outer surface of the outer catheter. The proximal end of catheter assembly 2 is in fluid communication with the interior volume of balloon 16 by way of annular lumen 18, and fluid channel 20. In some embodiments, inner catheter 6 may be located in an offset manner within outer catheter 4 such that the inflation lumen formed therebetween is crescent-shaped rather than annular.

The aforementioned disclosure enables a balloon microcatheter to be adapted to an optimal: small outer diameter for use in small vessels, flexibility to navigate in tortuous vasculature, high pressure tolerance to allow high flow rates of drug and contrast, short balloon inflation and deflation times, balloon bondability, balloon bond strength and maintenance of the balloon outer diameter to remain at or below the outer diameter of the outer catheter, even after balloon inflation and deflation.

Referring to FIG. 9, an axial cross section of a coaxial catheter assembly with outer catheter 4, inner catheter 6, inner catheter lumen 16 and annular lumen 18 defining a space between outer catheter 4 and inner catheter 6. Inner catheter lumen 16 extends from the proximal end of the outer catheter 4 to the distal end of the outer catheter 4 and allows fluid communication therebetween. Annular lumen 18 extends from the proximal end of the catheter assembly to the inner volume of a balloon and allows fluid communication to inflate and deflate the balloon.

Figures 10, 11A, 11B, 11C:
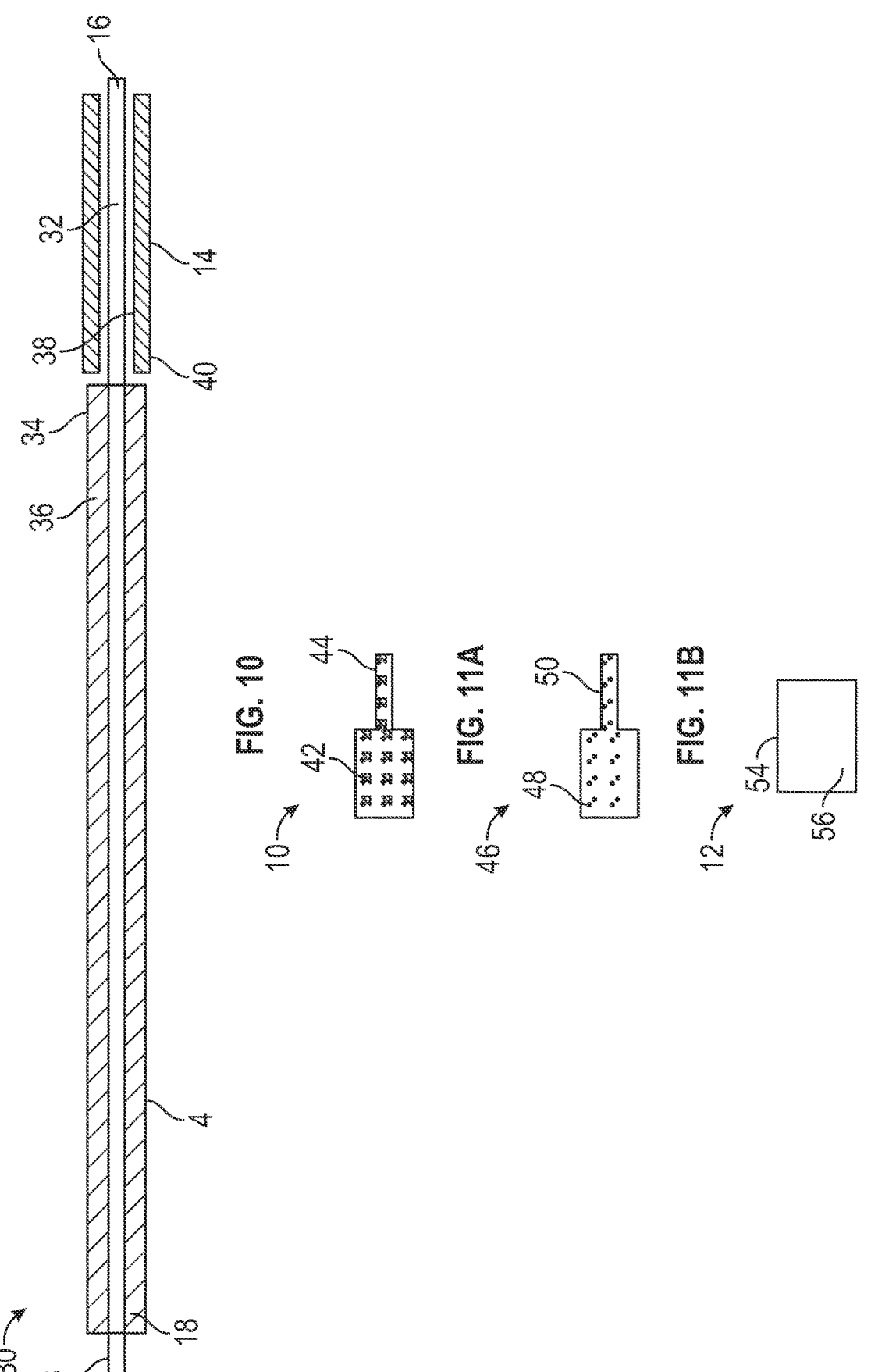
FIG. 10 is a longitudinal view of a coaxial catheter assembly.
FIG. 11A is a side view of an exemplary outer adapter.
FIG. 11B is a side view of an exemplary inner adapter.
FIG. 11C is a side view of a support sheath.

Referring to FIG. 10, a longitudinal cross section of catheter assembly 30 is shown with outer catheter 4, inner catheter 6, inner catheter lumen 16, annular lumen 18, inner catheter extension 32, external catheter surface 34, internal catheter surface 36 (i.e. a portion of the inside diameter of outer catheter 4), inner balloon surface 38 and outer balloon surface 40. Outer catheter 4 has a diameter greater than inner catheter 6 and has a length that is less than that of inner catheter 6. Annular lumen 18 defines a space between outer catheter 4 and inner catheter 6 and extends from the proximal end of catheter assembly 30 to the inner volume of balloon 14 and allows fluid communication to inflate and deflate the balloon. Inner catheter 6 has a length that is greater than that of outer catheter 4 and a lumen 16 that extends from the proximal end of catheter assembly 30 to the distal end of catheter assembly 30 and allows fluid communication therebetween. Inner catheter extension 32 with a diameter less than that of outer catheter 4, provides a surface whereby a balloon or other accessory can be attached with the bonding surfaces below the surface of (i.e. radially inward from the outside diameter of) outer catheter 4 and, if desired, the balloon or other accessory can be positioned such that its outer diameter is at or below the surface of outer catheter 4. In some embodiments, the balloon bonding surface may also be radially inward from the inside diameter of outer catheter 4. External catheter surface 34 defines a circumferential area on the outside of the distal end of outer catheter 4 whereupon adapters and sheaths may be affixed, and internal catheter surface 36 defines a circumferential area on the inside of the distal end of outer catheter 4 whereon adapters may be affixed. The diameters of external catheter surface 34 and internal catheter surface 36 are equal to the outer diameter and inner diameter of the catheter selected, respectively, typically from 0.3 mm to 5 mm, and the longitudinal length of the fixation surfaces can be from 0.2 mm to 25 mm, more typically from 1 mm to 10 mm.

Referring to FIG. 11A, a longitudinal cross section of an outer adapter 10 is shown with a diameter reduction between a large diameter surface 42 and a small diameter surface 44. Although outer adapter 10 shows a single step from large diameter surface 42 to small diameter surface 44, the transition can be configured with 2, 3, 4 or more steps or the transition can be a gradual as in a conical adapter. The outer adapter 10 provides a connection between the external catheter surface 34, of outer catheter 4 and an inner balloon surface 38 of balloon 14, providing fluid communication between the annular lumen 18 and the inner surface of balloon 14, whereby a proximal balloon bond is positioned between inner balloon surface 38 of balloon 14 and small diameter surface 44 of outer adapter 10, positioning the balloon bond below the surface of the outer diameter of outer catheter 4. In some embodiments, the outer adapter 10 (or any other adaptor herein) is made from a plastic polymeric material such as polyester, nylon, Pebax, polyethylene, polyurethane, or other convenient material. In many embodiments, a thin wall is preferred; however any thickness can be used depending on the application. Material thickness will typically range from 0.0016 mm to 0.025 mm, more typically from 0.003 mm to 0.015 mm. The large diameter surface 42 of outer adapter 10 is typically glued, heat bonded, compressed or reflowed into the external catheter surface 34 of outer catheter 4. Reflow has the advantage that large diameter surface 42 of outer adapter 10 melts into the outer surface of outer catheter 4 at external catheter surface 34 and does not increase the diameter of outer catheter 4. The diameters of the large diameter surface 42 and the small diameter surface 44 will be dependent on the catheter diameter and the desired positioning of the balloon bonding surface below the outer diameter of outer catheter 4. Typically the outer diameter of medical catheters range from about 0.25 mm to 10 mm, more typically from 0.5 mm to 5 mm, thereby making the large diameter surface 42 of the outer adapter 10 range from about 0.5 mm to 4 mm. The outside adapter 10 can be any length of convenience, typically 2 mm to 25 mm, more typically 4 mm to 10 mm. The outer adapter 10 of the present disclosure is particularly useful in micro-catheters that commonly have small outer diameters in the range of 0.5 mm to 1.5 mm and are used for access into the peripheral vasculature and into small blood vessels. In this instance, it is important to keep the outer diameter of the catheter as small as possible. If a balloon or other accessory is placed on the catheter, it can be a significant advantage to bond or otherwise mount the accessory below at least the outer surface of outer catheter 4. In addition to a balloon, an accessory can include a tissue anchor, blade, mechanical occlusion device, partial occlusion device, a device to trap embolic particles, or any device of use in the vasculature.

Referring to FIG. 11B, a longitudinal cross section of an inner adapter 46 is shown with a diameter reduction between a large diameter surface 48 and a small diameter surface 50. In any of the embodiments herein (if any adaptor is included), an inner adapter (e.g., inner adapter 46) can be used instead of outer adapter 10. Although inner adapter 46 shows a single step from large diameter surface 48 to small diameter surface 50, the transition can be configured with 2, 3, 4 or more steps or be a gradual transition as in a conical adapter. The inner adaptor has a proximal region 48 with an external surface that secured to inner catheter surface 36. The inner adapter provides a connection between the internal catheter surface 36 of an outer catheter 4 and balloon 14 at inner balloon surface 38, thereby positioning the balloon bonding surface or accessory attachment surface below the outer surface and the inner surface of outer catheter 4. The composition, measurements, use and benefits are as stated for FIG. 4A.

In some embodiments, an adaptor does not include a stepped region. For example, an adaptor can have a cylindrical configuration and coupled to inner surface 36, yet still provide a surface to which the proximal end of balloon can be bonded such that the bonding surface is below the OD of the outer catheter.

Referring now to FIG. 11C, a longitudinal cross section of exemplary support sheath 12 is shown with a proximal end, a distal end, an outer surface 54 and an inner surface 56. The support sheath 12 can fit circumferentially over the outer catheter 4 at external catheter surface 34 and balloon 14 at outer balloon surface 40. Support sheath 12 functions to strengthen the balloon bond and, if desired, hold the proximal end of balloon 14 at or below the outer surface of outer catheter 4. The length from proximal to distal ends of the support sheath is typically from 0.20 mm to 10 mm, more typically from 0.5 mm to 6 mm and any portion of the length can be bonded to the catheter with the remainder extended over the balloon or other accessory. In some embodiments, the support sheath has a length that is at least as great as the outside diameter of the distal end of the outer catheter. Typically the support sheath 12 is compressed, glued, reflowed or otherwise affixed to the outer catheter and extends over, but may not be attached to a balloon or other accessory. In some embodiments, the support sheath is made from polymeric material such as silicone, latex, polyester, nylon, Pebax, polyethylene, polyurethane, or other convenient material. In many embodiments, a thin wall is preferred, however, any thickness can be used depending on the application. In any of the embodiments herein, the support sheath can be a heat shrink material that is placed at a desired position over the catheter and balloon, or other accessory, and heated, causing the material to reduce in diameter and compress about the surface of the outer catheter and the balloon. The thickness will typically range from 0.003 mm to 0.05 mm, more typically from 0.006 mm to 0.01 mm. Reflow and compression have the advantage that the outer surface 54 of the support sheath 12 melts or is compressed into the outer surface of the outer catheter 4 and does not increase the diameter of the outer catheter. The diameter of support sheath 12 is dependent on the catheter diameter. Typically the outer diameter of medical catheters range from about 0.5 mm to 5 mm.

The sheaths herein may also be referred to as collars.

Figure 12A:
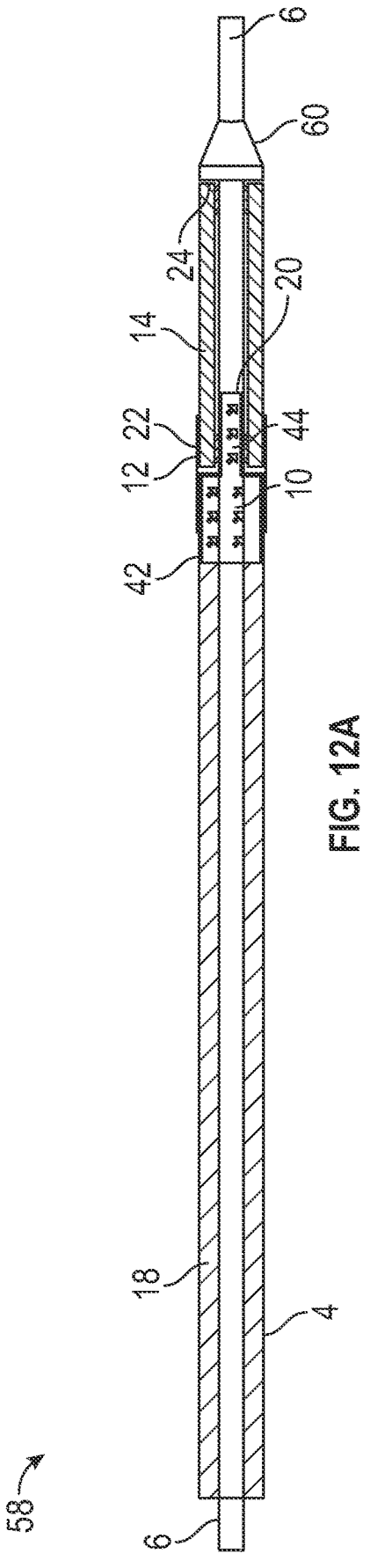
FIG. 12A is a longitudinal cross section of an exemplary embodiment that includes a nose cone.
Figure 12B:
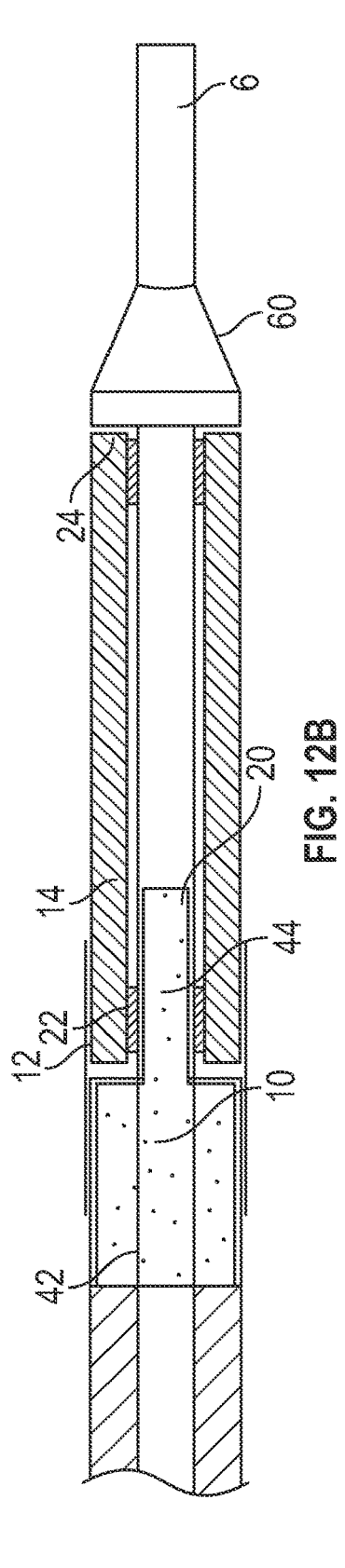
FIG. 12B is an enlarged view of the distal end of the catheter shown in FIG. 12A.

Referring now to FIGS. 12A and 12B, a longitudinal cross section of a second embodiment of the present disclosure is shown with catheter assembly 58, outer catheter 4, inner catheter 6, outer adapter 10, large diameter surface 42, small diameter surface 44, support sheath 12, nose cone 60, fluid channel 20, balloon 14, proximal balloon bond 22 and distal balloon bond 24. External catheter surface 34 of catheter 4 is bonded to the inner surface of the large diameter surface 42 of adapter 10. The inner surface of balloon 14 is bonded at its proximal end to the outer surface of small diameter surface 44 of adapter 10, at proximal balloon bond 22 and its distal end is bonded to inner catheter 6 at distal balloon bond 24 that is positioned proximal to nose cone 60. Support sheath 12 is positioned such that it extends over external catheter surface 34 of outer catheter 4 and the proximal end of balloon 14. The proximal end of support sheath 12 can be bonded, reflowed, compressed or otherwise affixed to external catheter surface 34 of outer catheter 4 and/or large diameter surface 42 of outer adapter 10, and the distal end of support sheath 12 is positioned over the proximal end of balloon 14 with the advantage of strengthening the balloon bond 22 and, if desired, holding balloon 14 below the surface of outer catheter 4. Support sheath 12 can be affixed to external catheter surface 34 and the proximal end of balloon 14, or it may not be affixed to one or both surfaces, provided that it does not move with respect to outer catheter 4 or balloon 14. Inner catheter 6 extends beyond the distal end of outer catheter 4 and nose cone 60 is affixed to inner catheter 6 at a location distal to the distal end of outer catheter 4. In this embodiment, the balloon sits in a pocket between the distal end of outer catheter 4 and the proximal end of nose cone 60 with the advantage of positioning the balloon bond lower than (i.e. radially inward from) the outer diameter of outer catheter 4 and, if desired, the balloon outer diameter, when in its unexpanded configuration, can be positioned so that it is substantially equal to or less than the outer diameter of the outer catheter 4. In this manner, a balloon, when in its unexpanded configuration, can be positioned within a pocket at or below the outer surface of outer catheter 4, expand to a diameter greater than outer catheter 4, and then return, upon deflation, to a diameter less than or equal to the outside diameter of outer catheter 4. The proximal end of catheter assembly 58 is in fluid communication with the interior space of balloon 14 by way of annular lumen 18 and adapter 10 at fluid channel 20 which is defined by an annular space between the inner surface of small diameter surface 44 of adapter 10 and the outer surface of inner catheter 6. Alternate configurations of this embodiment or any embodiment herein include use of adapter 10 and without the support sheath 12 or use of the support sheath 12 without the adapter 10. When only the support sheath 12 is used, the outer diameter of proximal balloon 14 is bonded to the inner surface of the support sheath 12. Another configuration of this embodiment includes the use of an outer adapter (not shown) to affix the balloon to the nose cone 60 or the use of a support sheath to affix balloon 14 to nose cone 60 or the use of both an adapter and support sheath to affix balloon 14 to nose cone 60. Optimally, balloon 14, adapters, support sheaths and none cone 60 have an outer diameter equal to or less than the outer diameter of outer catheter 4.

Figures 13A, 13B:
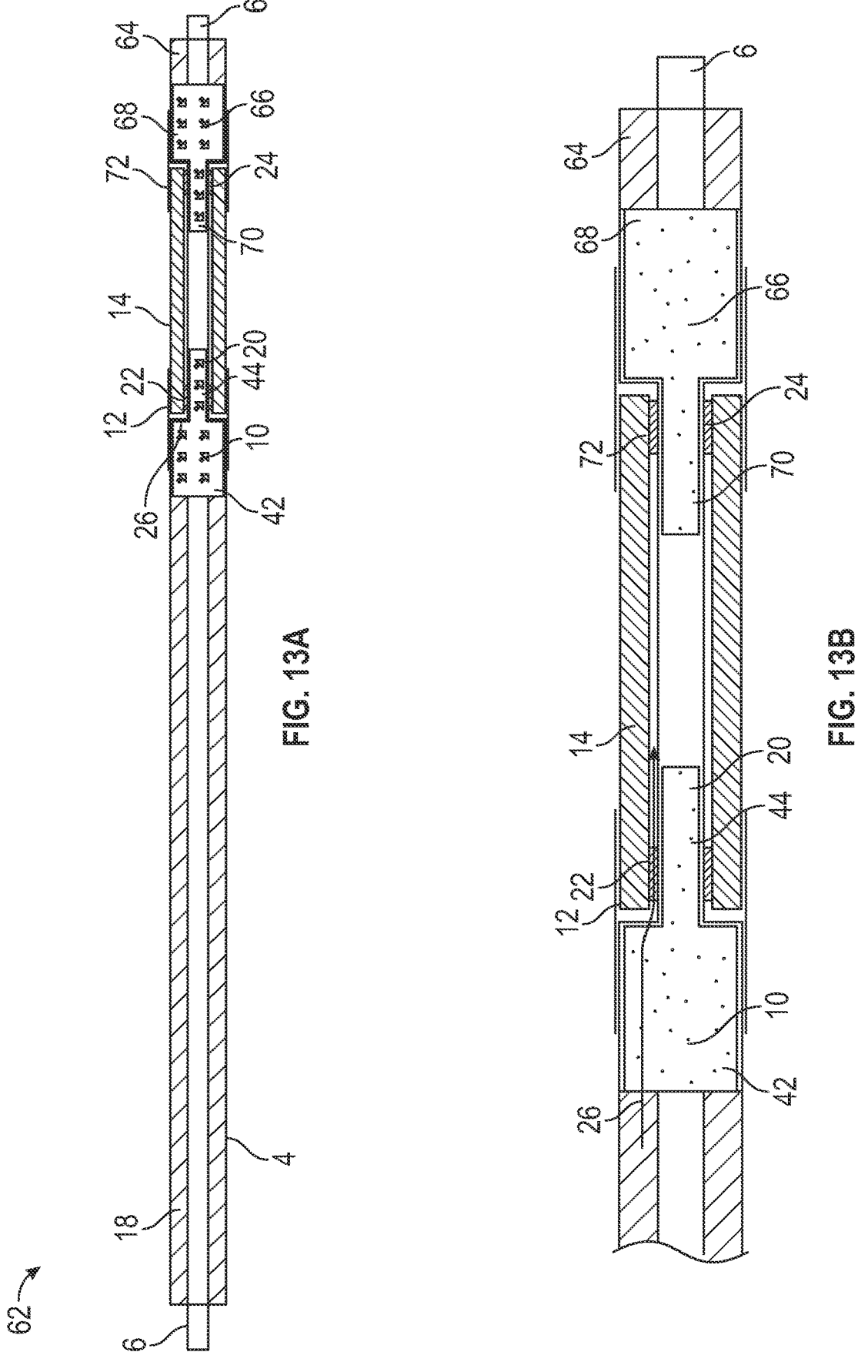
FIG. 13A is a longitudinal cross section of an exemplary embodiment including a second outer catheter.
FIG. 13B is an enlarged view of the distal end of the catheter shown in FIG. 13A.

Referring to FIGS. 13A and 13B, an exemplary embodiment of a device of the present disclosure is shown with catheter assembly 62, outer catheter 4, inner catheter 6, outer adapter 10, large diameter surface 42, small diameter surface 44, support sheath 12, fluid channel 20, balloon 14, proximal balloon bond 22, distal balloon bond 24, second outer catheter 64, distal outer adapter 66, large diameter surface 68, small diameter surface 70 and second support sheath 72. Inner catheter 6 extends beyond the distal end of outer catheter 4 and second outer catheter 64 may be affixed to inner catheter 6 at a location distal to the distal end of outer catheter 4, whereby balloon 14 is disposed in a pocket between the distal end of outer catheter 4 and the proximal end of second outer catheter 64 with proximal balloon bond 22 and distal balloon bond 24 positioned below the surface of outer catheter 4 and second outer catheter 64. In one construction of the present embodiment, balloon 14 is configured with an outer diameter less than or equal to the outer diameter of catheter 4 and second outer catheter 64 and thereby is concealed within a pocket therebetween. When inflated to its radially expanded configuration, balloon 14 will have a diameter greater than the outside diameters of outer catheter 4 and second outer catheter 64 and extend radially outward from said pocket. When balloon 14 is then deflated from its radially expanded configuration it will return to a diameter less than or equal to outer catheter 4 and second outer catheter 64 and again be concealed within the pocket. The external catheter surface 34 at the distal end of outer catheter 4 is bonded to the inner surface of large diameter surface 42 of adapter 10. The proximal end of balloon 14 is bonded at its inner surface to the outer surface of small diameter surface 44 of outer adapter 10 and the distal end of balloon 14 is bonded at its inner surface to the outer diameter of small diameter surface 70 of distal second adapter 66. Alternately, the inner luminal surface of balloon 14 can be bonded at its distal end directly to inner catheter 6. The inner diameter of large diameter surface 68 of distal adapter 66 is bonded, reflowed, compressed or otherwise affixed to the proximal end of a second outer catheter 64 or other distally extending structure, such as one or more shafts. A flow channel between the inner surface of small diameter surface 70 of second adapter 66 and inner catheter 6 may or may not be present. In the case where one balloon is present the distal end of the balloon will be sealed. However, if a second balloon is positioned distal to a first balloon, then a flow channel may be configured to allow inflation and deflation of a second, third, fourth or any number balloons and it is understood that any number of balloons and outer catheter segments can be positioned in series. A first support sheath 12 may be positioned such that it extends over the outer surface of the distal end of outer catheter 4 and the proximal end of balloon 14 and a second support sheath 72, may be positioned such that it extends over the outer surface of the proximal end of second outer catheter 64 and the distal end of balloon 14. Support sheaths 12 and 72 can be bonded, glued, reflowed, compressed or otherwise affixed to the distal end of outer catheter 4 or proximal end of second outer catheter 64 and may, if desired, be affixed to balloon 14. Support sheath 12 provides the advantage of restraining or compressing the proximal end of balloon 14 at the proximal balloon bond 22 and strengthening the balloon bond and preventing detachment. A second support sheath 72 adds the advantage of retaining or compressing balloon 14 at distal balloon bond 24 or strengthening the balloon bond and preventing detachment.

In any of the embodiments herein that include one or more support sheaths (collars), any of the those collars may be replaced with any other suitable sheath/collar described herein.

The proximal end of catheter assembly 62 is in fluid communication with the interior space of balloon 14 by way of annular lumen 18 and outside adapter 10 at fluid channel

20, which is defined by an annular space between the inner surface of small diameter surface 44 of adapter 10 and the outer surface of inner catheter 6 as seen by flow path 26. Alternate configurations of this embodiment include an outer adapter 10 without a support sheath 12, a support sheath 12 without adapter 10, outer adapter 66 without second support sheath 72, second support sheath 72 without outer adapter 66 or any combination of adapters and support sheaths, provided that the proximal end and distal end of balloon 14 have at least one adapter or sheath or are bonded directly to inner catheter 6 and annular lumen 18 is in fluid communication with the interior surface of balloon 14. Optionally, balloon 14, both support sheaths and both adapters have an outer diameter equal to or less than the outer diameters of outer catheter 4 and second outer catheter 64 of catheter assembly 62, although there is no requirement for balloon 14 to be constrained below the surface of catheter assembly 62, provided that bonding surfaces 22 and/or 24 are positioned below the outer surface of catheter assembly 62. It would be particularly useful when delivering therapy in small vessels, for a balloon or other accessory or tool to be positioned below the surface of a catheter, in its unexpanded state, and then following inflation or deployment be returned to the same position below the catheter surface.

Figures 14A, 14B:
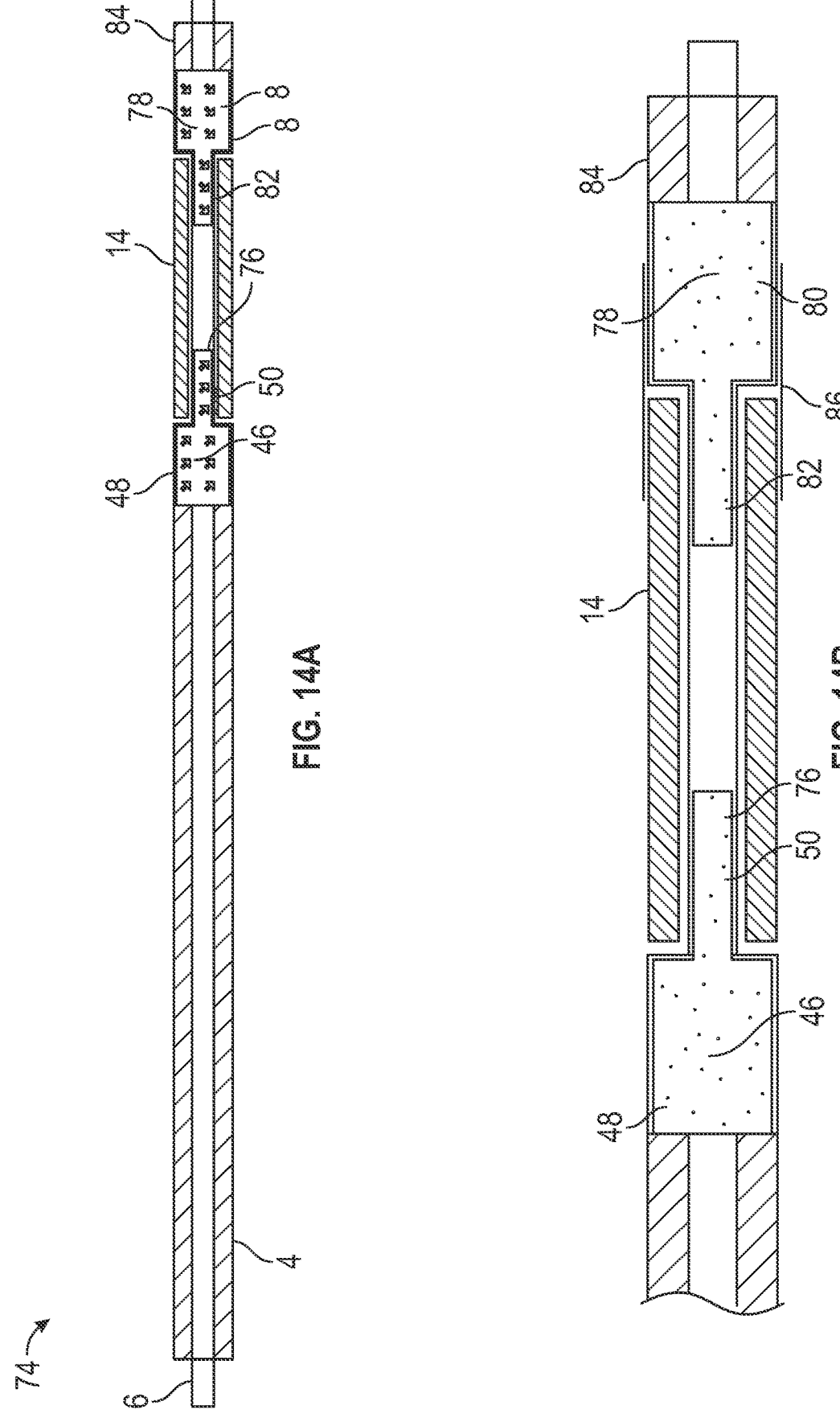
FIG. 14A is a longitudinal cross section of an embodiment of the present disclosure including an inner adapter.
FIG. 14B is an enlarged view of the distal end of the catheter shown in FIG. 14A.

Referring now to FIGS. 14A and 14B, a longitudinal cross section of yet another exemplary embodiment of the present disclosure is shown with catheter assembly 74, outer catheter 4, inner catheter 6, proximal inner adapter 46, large diameter surface 48, small diameter surface 50, fluid channel 76, distal inner adapter 78, large diameter surface 80, small diameter surface 82 and support sheath 86. In this embodiment, inner adapters 46 and 78 are used instead of outer adapters whereby the outer surfaces of large diameter surfaces 48 and 80 of inner adapters 46 and 78 are bonded or otherwise affixed to the inner circumference of outer catheter 4 and the inner circumference of second outer catheter 84. In this embodiment, the balloon 14 is disposed in a pocket between the distal end of outer catheter 4 and the proximal end of second outer catheter 84 (or other distally extending structure, such as one or more shafts). It is understood that any combination of adapters and support sheaths can be used. For example, an outer adaptor can be replaced with an inner adaptor. The proximal and/or distal balloon bonds are positioned below the outer surfaces of outer catheter 4 and second outer catheter 84 and fluid communication is maintained from the proximal end of catheter assembly 74 and the interior surface of the balloon 14 by way of annular lumen 18 and adapter 46 at fluid channel 76 which is defined by an annular space between the inner surface of small diameter surface 50 of adapter 46 and the outer surface of inner catheter 6. It is also understood that a nose cone or other nose piece can be affixed to a location distal to the second outer catheter 84 and that any number of balloons and outer catheter segments can be serially oriented along catheter assembly 74.

Figures 15A, 15B:
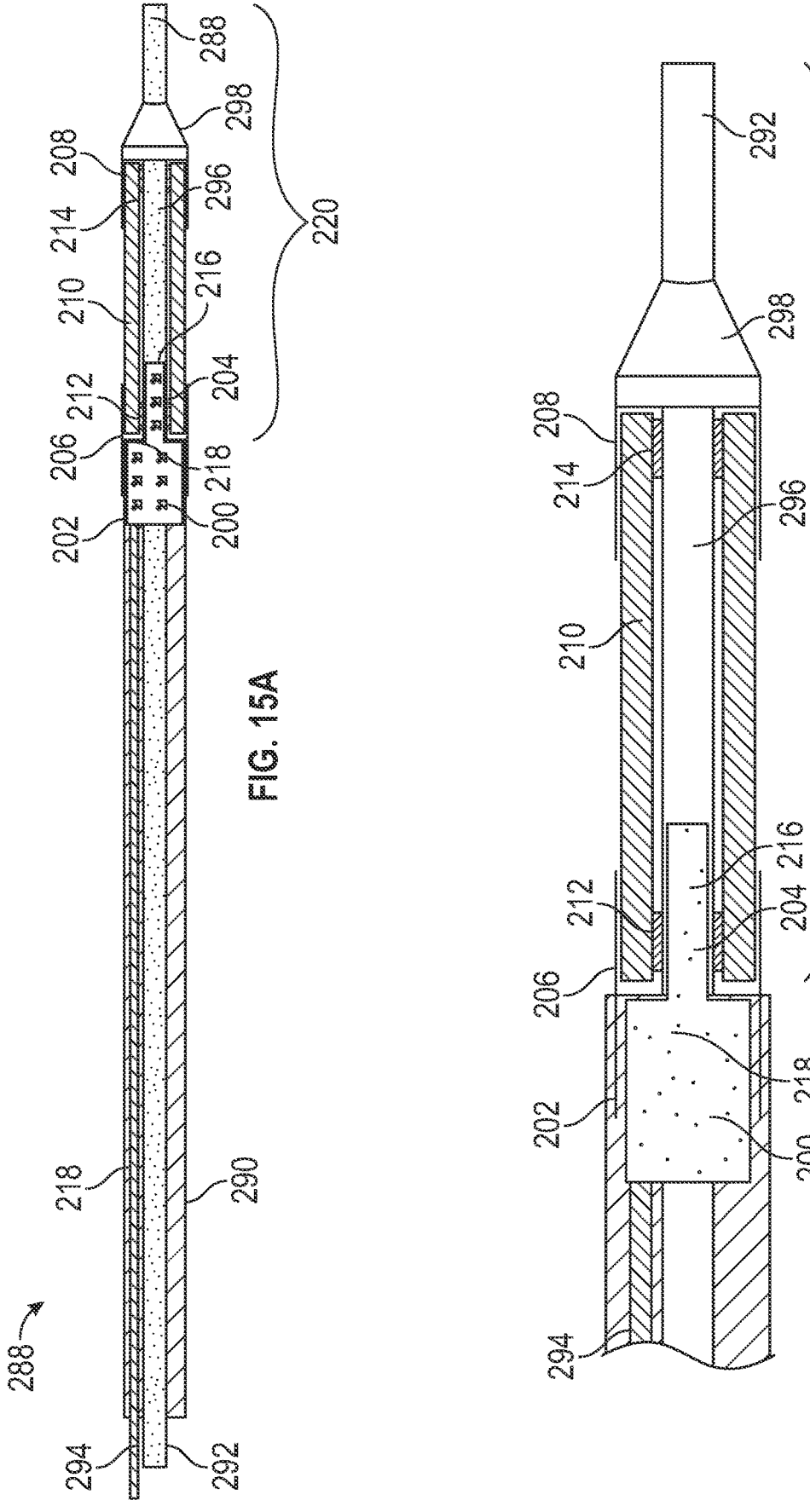
FIG. 15A is a longitudinal cross section of a fourth embodiment of the present disclosure including a two lumen catheter.
FIG. 15B is an enlarged view of the distal end of the catheter shown in FIG. 15A.

Referring now to FIGS. 15A and 15B, yet another exemplary embodiment of the present disclosure is shown with catheter assembly 288, two lumen catheter 290, injection lumen 292, balloon inflation lumen 294, injection lumen extension 296, nose cone 298, outer adapter 200, large diameter surface 202, small diameter surface 204, support sheaths 206 and 208, balloon 210, proximal balloon bond 212, distal balloon bond 214, fluid channel 216 and flow path 218. In this instance, a single catheter with two lumens is used instead of the two catheter coaxial construction as described in the above embodiments. While a two lumen catheter is useful for numerous applications, the catheter can also include 3, 4, 5 or more lumens as needed. Catheter assembly 288 can be any length useful for medical applications, typically from 25 cm to 250 cm, more typically from 50 cm to 150 cm. Injection lumen 292 has a proximal end and a distal end and extends from the proximal end of catheter assembly 288 to the distal end of catheter assembly 288 and provides fluid communication therebetween. Balloon inflation lumen 294, has proximal and distal ends and extends from the proximal end of catheter assembly 288 to balloon 210, providing a means for inflation and deflation. Injection lumen 292 extends distally beyond the distal end of two lumen catheter 290 and distally beyond the end of balloon lumen 294 as illustrated by injection lumen extension 296 and length 220. The injection lumen extension typically has a length in the range of 0.1 cm to 50 cm, more typically from 1 cm to 10 cm. Nose cone 298 is positioned about the injection lumen extension 296 at a point that is distal to the distal end of two lumen catheter 290, whereby balloon 210 is disposed in a pocket between the distal end of two lumen catheter 290 and the proximal end of nose cone 298. Nose cone 298 is typically placed at a distance of 0.25 cm to 10 cm, more typically from 1 cm to 3 cm from the distal end of two lumen catheter 290 and can be any shape or configuration and can be composed of any convenient material including materials that are radiopaque. For illustration only, the embodiment of FIGS. 15A and 15B includes outer adapter 200 and both proximal and distal support sheaths 206 and 208, however any combination of adapters and support sheaths can be used, provided that fluid communication is maintained between the inflation lumen 294 and the interior surface of balloon 210. Outer adapter 200 has a large diameter surface 202 and a small diameter surface 204, whereby the inner surface of large diameter surface 202 is bonded to the distal outer surface of two lumen catheter 290 and the small diameter surface is oriented about injection lumen extension 296, such that an annular space between the inner surface of small diameter surface 204 and injection lumen extension 296 is maintained. The proximal end the catheter assembly 288 is in fluid communication with the interior space of balloon 210 by way of balloon inflation lumen 294, outer adapter 200, an annular space between the injection lumen extension 296 and the inner surface of the small diameter surface 204 of adapter 200, defined by fluid channel 216 and flow path 218. In most cases it is desirable that the central injection lumen 292 allow fluid communication therethrough, however, this is not a requirement. In some uses, the injection lumen 292 can be a solid and without fluid communication, thereby configuring a one lumen balloon catheter. It may also be desirable for balloon 210 to sit below the outer diameter of catheter assembly 288, however this is not required. In some embodiments, balloon 210 does not sit below the outer diameter of catheter assembly 288, but at least the proximal balloon bond 212 is positioned below the outer diameter of catheter assembly 288.

In any of the embodiments herein that include a balloon, the balloon may comprise a silicone material, and may optionally consist essentially of a silicone material. Using one or more silicone materials for the balloon can provide more elasticity, which can allow the balloon to return to an unexpanded configuration that is at or below the OD of the outer catheter.

The material that is used in a balloon, such as a silicone, may, however, present challenges in that it may be difficult to bond the balloon to other surfaces relying solely on an adhesive, solvent or heat. In any of the embodiments herein, a surface to which a balloon surface is bonded (i.e., secured) may include one or more surface features that are adapted and configured to increase the stability between the balloon surface and the surface to which the balloon surface is bonded.

The one or more surface features may be on any of the adaptors herein, such as any of the proximal adaptors herein or any of the distal adaptors herein. The one or more surface features may be present on the entire length of the adaptor, or they may be present on less than the entire adaptor, such as only where a balloon surface is to be bonded. For example, in the adaptor shown in FIG. 11A, the one or more surface features may be present only on the outer surface 44 in the smaller diameter distal region. For example, in the adaptor shown in FIG. 11B, the one or more surface features may be present only on the outer surface 50 in the distal region. Or even if the adaptor does not have a step (e.g., has a cylindrical configuration), the one or more surface features may only be on a distal region of the adaptor, and may be only an outer surface of the distal region. The same concepts apply to any distal adaptor that may be used herein, while it will be understood that the one or more surface features may be disposed only a proximal region of the adaptor, such as where a balloon might be bonded thereto (regardless of the configuration of the adaptor).

The one or more surface features can include a wide variety of features that are adapted and/or configured to increase friction and/or increase the stability between the one or more features and a balloon surface.

In some embodiments a surface feature can include raised regions on the surface.

In some embodiments a surface feature can include one or more textured features.

In some embodiments a surface feature can include a non-smooth surface that is configured to increase the friction with a balloon surface.

In some embodiments a surface feature can include one or more barbs.

In some embodiments a surface feature can include one or more sharpened features.

Any particular surface may include more than one type of surface feature. For example only, a surface may include one or more raised regions and one or more sharpened features.

One or more surface features may be created in the surface to which the balloon is bonded using a variety of techniques that can create a textured, roughened, and/or non-smooth surface. For example without limitation, a surface can be exposed to any number of solvents or abrasive materials to create a textured surface. The process may be performed mechanically, chemically, and/or optically, for example.

In any of the embodiments herein, a material may also be deposited on the surface of the adaptor, collar, and/or inner catheter (or any other surface to which a balloon surface may be bonded) that is adapted to increase the stability of the balloon relative to the surface. In these embodiments, the balloon surface may only make contact with the material, or it may make contact with the material as well as the structural component (e.g., adaptor, collar, and/or inner catheter, for example). A material may be deposited on the surface to increase the stability, and the surface may also include any of the one or more surface features that are adapted to increase stability. For example without limitation, a material that may be deposited onto the surface may be an adhesive that results in an increase in friction, even if the adhesive does not create strong adhesive forces with the balloon material (e.g., silicone) as generally occurs with typical adhesives.

Figures 16A, 16B:
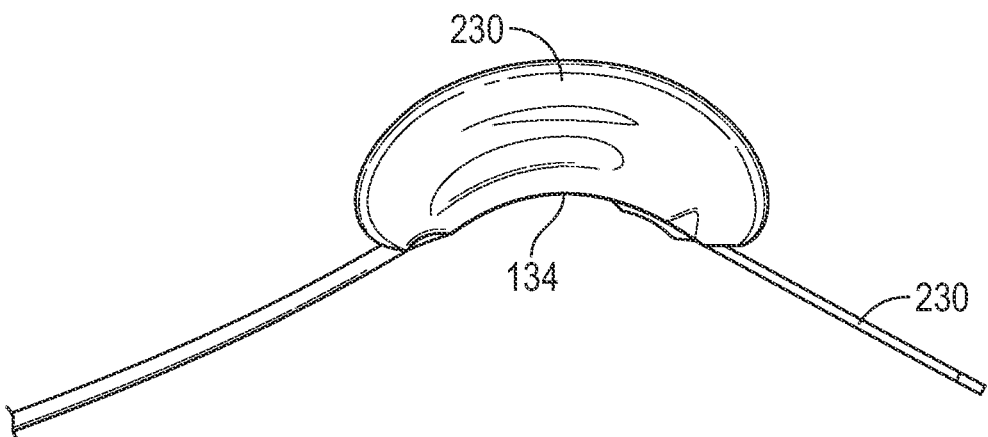
FIG. 16A is a side view of a catheter balloon inflated to the extent that it laterally deflects the distal tip of the catheter for steering.
FIG. 16B is the same as FIG. 16A with markings added to show various deflection angles.

Referring now to FIGS. 16A and 16B, an embodiment is shown comprising a balloon mediated steerable catheter. As shown in FIG. 16A, a catheter tip may be provided with a balloon 230 near its distal tip 232, similar or identical to the configurations previously described. The balloon 230 may be inflated as shown past a diameter needed to occlude a small blood vessel such that it bulges laterally to one side of the catheter tip 232 as shown. This off-center state of balloon 230 forces the distal tip 232 of the catheter to bend laterally in the opposite direction around a "bend point" 234. The degree of bend or bend angle of distal tip 232 is a function of the volume of fluid in balloon 230. This arrangement can be used as a means to steer a catheter around a sharp turn.

FIG. 16B depicts various angles that catheter tip 232 may bend away from the longitudinal axis of the main catheter. As balloon 230 is progressively inflated with more fluid, tip 232 may bend from a straight orientation (a) through various acute angles (b), (c) and (d), to a right angle (e) and to obtuse angles (f) and (g), as shown.

According to some exemplary embodiments, a protocol for advancing a catheter around a sharp turn may comprises one or more of the following steps:

1) track the catheter over a guidewire to the vascular branch or sharp angle;
2) withdraw the guidewire just enough to position the distal tip of the guidewire to a position proximal to the catheter bend point 234;
3) inflate the balloon 230 and visualize the direction that the catheter tip 232 is bending, such as by using fluoroscopy;
4) rotate the catheter axially such that tip 232 is pointed in the desired direction;
5) further inflate or deflate balloon 230 until catheter tip 232 is pointed into the desired branch artery;
6) advance the guidewire into the branch artery;
7) advance the catheter over the guidewire into the branch artery; and
8) deflate the balloon and continue to advance the catheter over the guidewire.

In some protocols, a contrast agent can be injected through the distal tip 232 of the catheter and fluoroscopy can be used to visualize the target vessel.

Balloon 230 may be configured with a uniform wall thickness, or it may be provided with a thinner wall thickness on one side to ensure that it inflates laterally to the same side every time. In some embodiments, the wall thickness may be varied to provide a desired shape or inflation profile. In some embodiments the balloon is configured to surround the circumference of the catheter, and in other embodiments it can be attached to only one side of the catheter. In embodiments that utilize a balloon that surrounds the catheter, an adhesive may be used between one side of the catheter and part of the inside surface of the balloon to ensure that the balloon does not inflate on that side.

In some embodiments, bend point 234 is the midpoint of a curve. The curve may have a radius of 50 mm, 25 mm, 10 mm or less. The catheter may be modified at bend point 234 to allow the catheter to bend with less force applied by balloon 230. For example, the catheter may have a reduced diameter and/or wall thickness at one or more locations to facilitate easier bending and/or a smaller radius of curvature. In some embodiments, the bend point can be varied by advancing or retracting a guidewire within the catheter, such that the catheter starts bending just beyond the distal end of the guidewire.

Any of the embodiments herein may also include a shaped tip, examples of which are described below.

Described herein are catheter designs that allow a shaped tip to be more easily navigated through tortuous vasculature. Termination of the catheter at a flexible, soft tip is desirable to minimize vessel trauma. The added support of a rigid section in proximity to the distal tip further aides in catheter tracking as a flexible section (without support or reinforcement) would be prone to kink and excessive flexing.

Referring to FIGS. 17A-17E, various exemplary shaped tips are schematically shown. In each of these examples, two or more layers of tubing are combined to create the tip construct. The left side of each figure represents the proximal end of the shaped tip, which may be connected to the distal end of any inner catheter herein (e.g., inner catheter 112 as shown in FIGS. 3A-3B), and the right side of each figure represents the distal end of the shaped tip. Reference letters A-F and W denote discrete pieces of tubing which in some embodiments are each formed from different materials. The base material of tube A is formulated to bond to the main body of the catheter. W denotes a tube comprising tungsten, or in some embodiments another radio opaque material that serves as a location marker under fluoroscopy or other imaging during a surgical procedure. In other embodiments, W may simply denote another material similar to the materials of A-F (i.e. not having any special radio opaque properties.) The shaped tips disclosed herein may be used at the distal end of catheters with or without balloons.

Figure 17A:
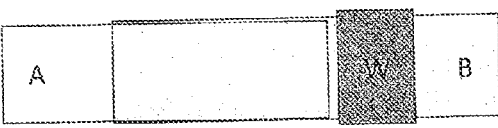
FIGS. 17A, 17B, 17C, 17D and 17E are a series of side views schematically showing various exemplary shaped tips.

In the construct depicted in FIG. 17A, a tube A comprising a first polymeric material (such as a polyether block amide, or PEBA) is placed within a tube B comprising a second polymeric material (which may also be a PEBA.) In this embodiment, the material of tube B is softer, more flexible and has a lower durometer than the material of tube A. Tube W, comprising tungsten, is placed over the distal end of tube B and located just distal to the middle region where tubes A and B are overlapping.

Tube A may be oversized so that its proximal end slides over the distal end of an inner catheter. Heating tube A (before or after tubes B and W are added) allows tube A to shrink to fit over an inner catheter. The three tubes A, B and W may then be heated to melt and bond together and to the inner catheter using a material reflow process. The multiple layers may be processed in parallel or in series. In the middle section of FIG. 17A where tubes A and B overlap, the materials of tubes A and B may blend together in the reflow process such that the middle section no longer has discrete layers but rather comprises a blend of materials. Temperature profiles, time and other parameters of the shrink to fit and/or reflow process may vary based on material selection, diameter and thickness. In some embodiments, materials A, B and W each have a different color which may blend together during the reflow process or may remain distinct. With this disclosed fabrication method, material selection and layering can create different bend profiles of the shaped tip, offering transition from rigid to flexible in a gradient rather than abrupt transition(s), which can reduce kinking of the catheter tip. The construct depicted in FIG. 17A includes the characteristics of having a strong hold to its shape, relatively thick walls, and a radio opaque marker near its distal tip, but can be difficult to manufacture.

Figure 17B:
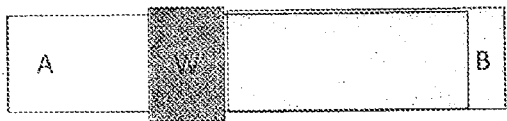

Referring to FIG. 17B, a shaped tip similar to the construct shown in FIG. 17A is provided. In this example, the region of overlap between tubes A and B is longer, the length which tube B extends distally from the overlap region is shorter, and tube W is located proximal to the overlap region rather than distal to it as in the example shown in FIG. 17A. The construct depicted in FIG. 17B includes the characteristics of having a good hold to its shape, relatively thick walls, a radio opaque marker away from its distal tip, and is less difficult to manufacture than the tip shown in FIG. 17A.

Figure 17C:
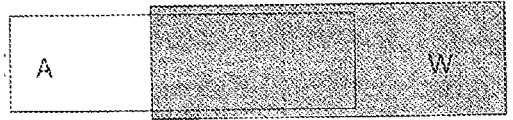

Referring to FIG. 17C, a shaped tip similar to the construct shown in FIG. 17A is provided. In this example, there are only two tubes used: A and W. Instead of having only a narrow marker band W as shown in FIG. 17A, the entire distal tube W may comprise a radio opaque material such as tungsten, as shown in FIG. 17C. In this exemplary embodiment, the material of tube W is softer, more flexible and has a lower durometer than the material of tube A. The construct depicted in FIG. 17C includes the characteristics of having a good hold to its shape, a radio opaque marker that extends to its distal tip, has less of a flexibility/rigidity gradient, and is fairly easy to manufacture compared with the previously described tips.

Figure 17D:
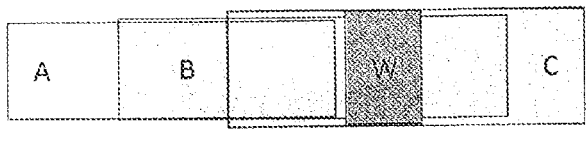

Referring to FIG. 17D, a shaped tip similar to the construct shown in FIG. 17A is provided. In this example, a forth material C is used. Each of the materials A, B and C gets progressively softer, more flexible and has a lower durometer moving distally. As depicted in FIG. 17D, there are six regions of the shaped tip of this embodiment (proximal to distal): A, A+B, A+B+C, B+C+W, B+C and C.

Figure 17E:
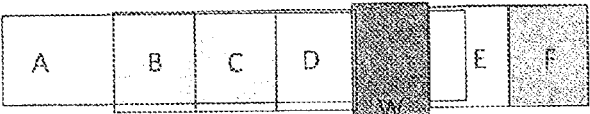

Referring to FIG. 17E, a shaped tip similar to the construct shown in FIG. 17C is provided. In this example, seven materials are used. Each of the materials A, B, C, D, E, and F gets progressively softer, more flexible and has a lower durometer moving distally. As depicted in FIG. 17E, there are eight regions of the shaped tip of this embodiment (proximal to distal): A, A+B, A+C, A+D, A+W, A+E, E and F. Tubes B, C and D abut rather than overlap with one another, as do tubes E and F. Since tube A extends only partway through tube E in this embodiment, tubes E and F may be temporarily mounted over a mandrel when fusing them together to ensure proper alignment. The constructs of FIGS. 17D and 17E have more of a flexibility/rigidity gradient than the previously described embodiments. Material wall thicknesses may also be varied to further tune performance and behavior of the tip.

In the exemplary embodiments depicted in FIGS. 17A-17E, when there is an overlapping joint rather than a butt joint between two tubes, the more distal of the two tubes slides over the more proximal tube. This is done so that if an edge of the outer (distal) tube remains after the manufacture of the shaped tip is complete, it will not impede the insertion of the tip into a patient's vasculature. If such an outer edge does remain after manufacture, it may increase friction and/or catch on features of tortuous vasculature when the shaped tip is being withdrawn with the catheter from the patient. However, this is less of an issue during removal of the catheter because the catheter is in tension during removal, as opposed to being in compression during insertion when the catheter may tend to buckle rather than advance through the vasculature. In alterative embodiments (not shown), the more proximal of the two tubes may be slid over the more distal tube during manufacture.

Figure 18:
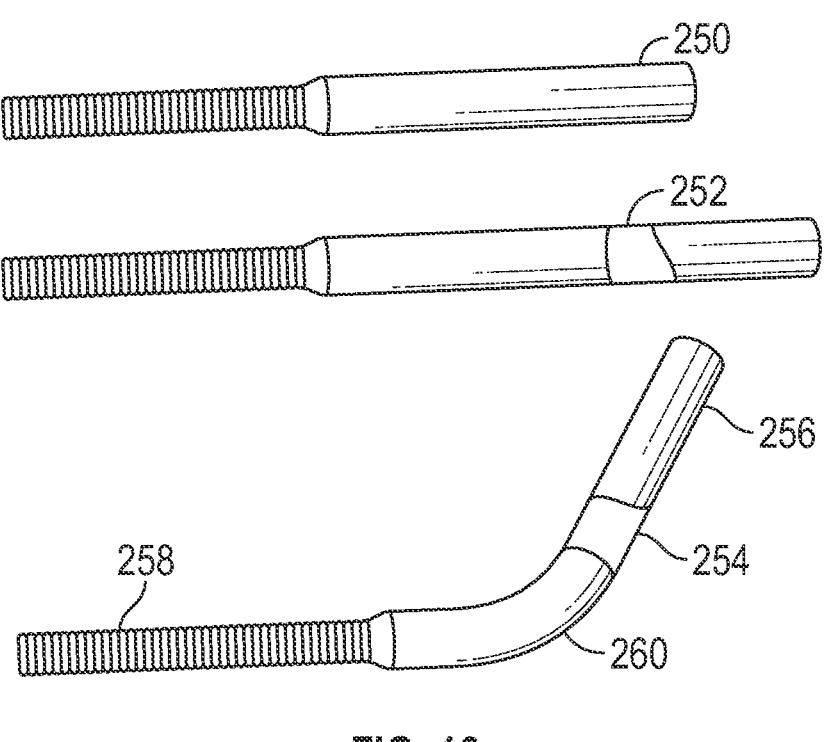
FIG. 18 is a plan view showing three catheter tips in various stages of manufacture.

Referring to FIG. 18, three catheter tips are shown in various stages of manufacture. All three tips are formed using a layering process similar to that shown in FIG. 17A as previously described. Catheter tip 250 uses materials that are generally the same color so that the various layers are not readily apparent after they have been reflowed together. Tip 252 uses materials A, W and B that each have a different color. In some embodiments such as this, the material colors remain distinct after the reflow process. In other embodiments (not shown), colors of the various overlapping materials blend together such that the distinct tube materials are no longer readily discernable.

After a straight catheter tip is formed, such as previously described, it may be shaped into a non-straight configuration. For example, tip 250 shown in FIG. 18 may be used in its straight configuration while tip 252 may be formed into a curved tip 254 as shown. A low temperature may be used to set the material to a desired shape after the reflow process described above. Holding the material in the desired shape while at a temperature that is below the reflow temperature, such as 225 degrees F. for approximately 120-180 seconds for a layered construct of PEBA tubes, can change the overall shape of the tip without altering its dimensional aspects. These temperature and time parameters work for a convection based technique after a shaping mandrel having the desired shape is inserted through the distal end of the central lumen of the tip. An outer mold or tool with the desired shape may be used instead of or in conjunction with the mandrel. If the tip is in contact with media other than air, the temperature may need to be adjusted to ensure no dimensional changes occur during the shape changing process. For example, if the tip is held in a glass or aluminum fixture, etc., a temperature of 110-150 F may be needed, and it may be held at this temperature for less time. As shown in FIG. 18, the shaped tip 254 of this exemplary embodiment has a straight distal portion 256 configured to deviate from the longitudinal axis of the main body 258 of the catheter when tip 254 is in its relaxed state. The straight distal portion 256 extends through an angle of about 70 degrees from the longitudinal axis. A curved portion 260 may be provided between straight distal portion 256 and main body 258 as shown. In this exemplary embodiment, curved portion 260 has an inside bend radius of about 0.10 inches, or about 3 times the outside diameter of the tubing forming the tip 254. This tight bend radius allows the catheter tip to be maneuvered through tighter turns in the vasculature. In other embodiments, the bend radius may be smaller or larger. In some embodiments, the bend radius is no smaller than about 0.015 inches, as a bend radius smaller than this in a tube of the same diameter is difficult to traverse with a guidewire.

Figure 19:
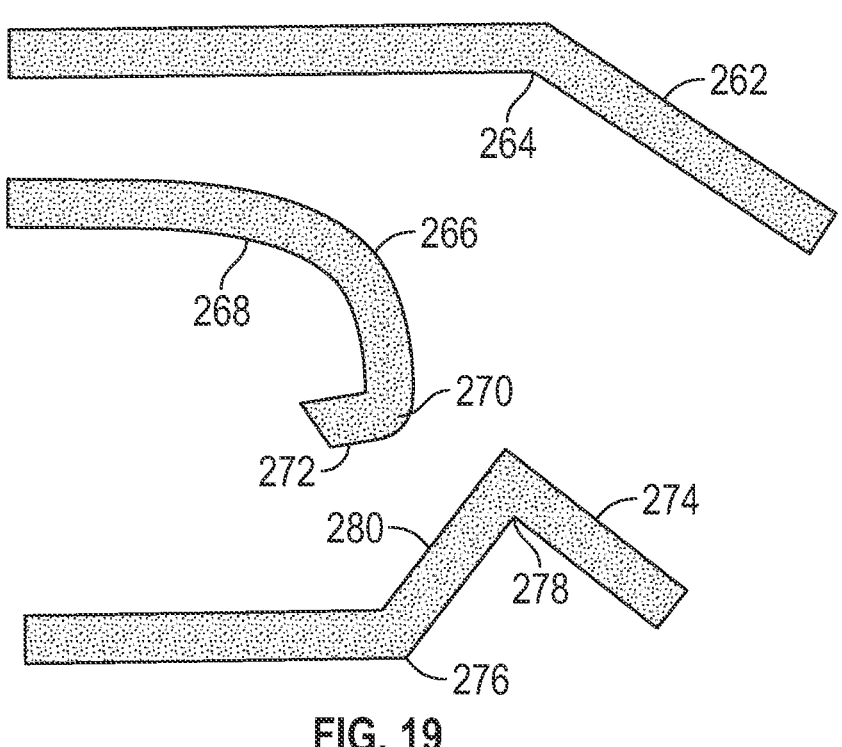
FIG. 19 is a plan view schematically showing three more examples of shaped catheter tips.

Referring to FIG. 19, three more examples of shaped catheter tips are schematically shown. Tip 262 is similar to tip 254 in FIG. 18, but has a sharper bend 264. Tip 266 includes three bends 268, 270 and 272. First bend 268 has a bend radius that becomes increasingly smaller towards the distal tip. Second bend 270 has a tighter bend radius in the same direction as first bend 268. Together, bends 268 and 270 turn tip 266 about 180 degrees, forming a hook shape. Third bend 272 has a bend radius that is larger than those of bends 268 and 270, and bends in the opposite direction. Tip 274 includes two sharp bends 276 and 278, each bending in opposite directions and separated by a straight section 280. Various other combinations of single or multiple bend shaped tips are possible using the manufacturing techniques disclosed herein. For example, a J-shaped tip similar to tip 266 may have a single, continuous bend of constant radius and may extend 180 degrees, between 120 and 160 degrees, or other angle.

Figures 20A, 20B, 20C, 20D:
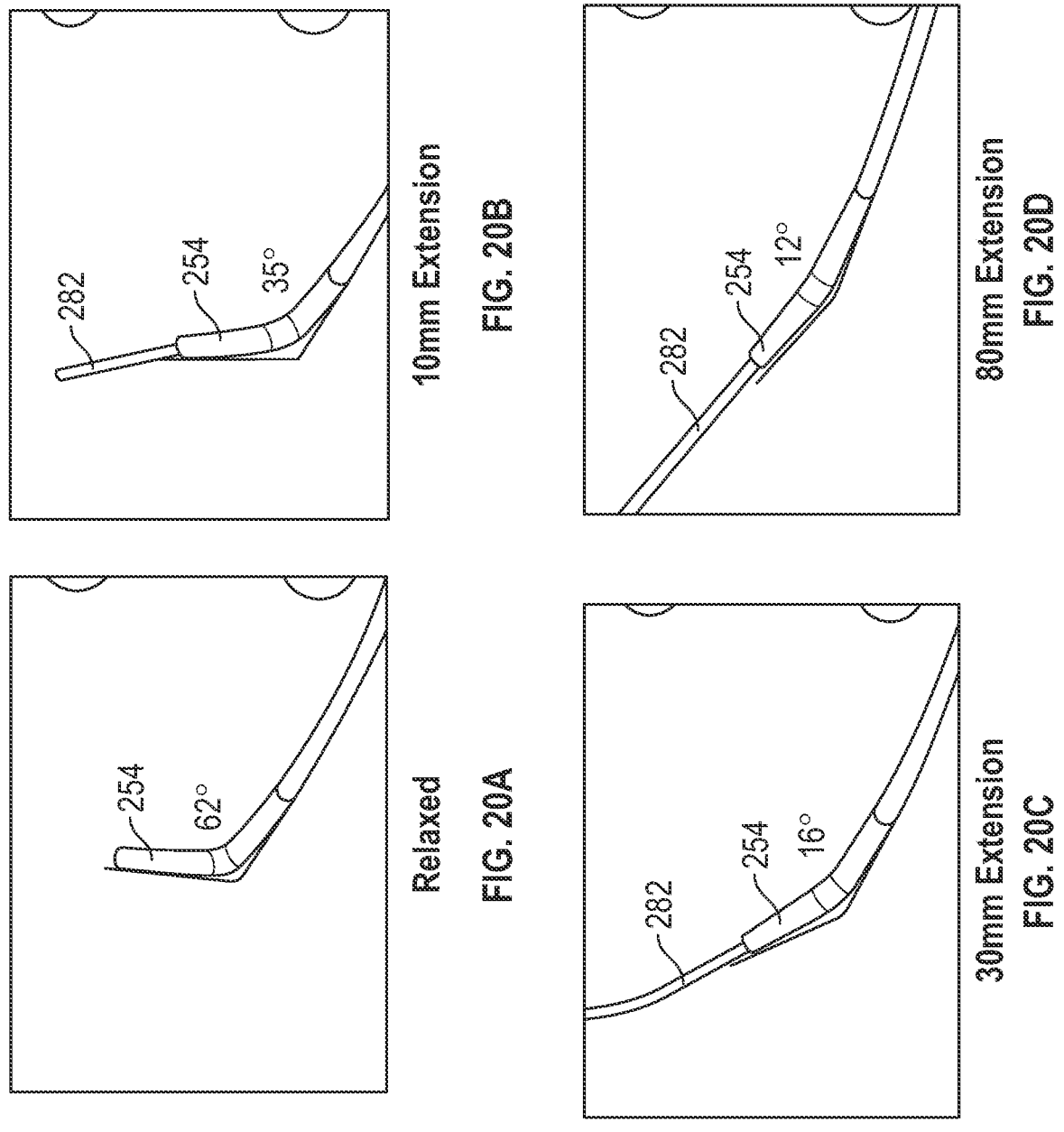
FIGS. 20A, 20B, 20C and 20D, are a series of plan views showing a shaped tip being progressively straightened by advancing a guidewire through it.

Referring to FIGS. 20A-20D, a series of images are provided showing shaped tip 254 progressively straightened by advancing a guidewire through it. As previously described, the catheter and shaped tip 254 are provided with a central lumen configured to receive a flexible guidewire 282. FIG. 20A shows shaped tip 254 in a relaxed state and having a deflection angle of 62 degrees. When the distal tip of guidewire 282 is passed through shaped tip 254 as shown in FIG. 20B, the stiffness of guidewire 254 causes tip 254 to move towards a straighter configuration (i.e. to have an angle of deviation of less than 62 degrees from the longitudinal axis of the main body 258), such as 35 degrees in this case. A guidewire may be used that increases in stiffness moving from its distal end towards its proximal end. When such a guidewire 282 is advanced further through tip 254, it causes tip 254 to further straighten towards the longitudinal axis of the catheter. In this exemplary embodiment, a 10 mm extension of guidewire 282 through tip 254 causes it to straighten to 35 degrees as shown in FIG. 20B, an extension of 30 mm causes an angle of 16 degrees as shown in FIG. 20C, and an extension of 80 mm causes an angle of 12 degrees as shown in FIG. 20D. A surgeon can thus steer tip 254 through turns in a patient's vasculature by adjusting the angle of the tip with the depth of guidewire 282.

Prior art shaped tips are typically made of a single material and often have lengths between about 1.5 and 3.0 cm in length. Using the fabrication techniques disclosed herein, similar bend profiles can be achieved in a shorter distance. In some embodiments, the lengths of the inventive tips extending beyond the base catheter are between 0.3 and 1.0 cm. These shorter lengths allow for the catheter to be maneuvered through tighter turns in the vasculature while minimizing the distance from the distal tip of the catheter to an operational interface such as a balloon. This allows accurate positioning of the operational interface and distal tip for the desired application, such as therapeutic delivery.

In one particular exemplary embodiment, a shaped tip is formed from two Pebax tubes in a starting configuration similar to that shown in FIG. 17C. Tube A is made of a 35 durometer Pebax infused with 40% barium sulfate to increase lubricity. A stabilizer may also be added so the material can withstand higher temperatures for longer periods of time, and longer exposure to ultraviolet/fluorescent light. In this embodiment, the inside diameter of tube A is 0.031"±0.0005", the wall thickness is 0.004"±0.0005", the concentricity is ≥85% and the length is 4.0 mm. Tube W is made of 25 durometer Pebax infused with 70% tungsten by weight. A stabilizer may also be added to tube W. The inside diameter, wall thickness, tolerances and length for tube W are the same as for tube A.

In some exemplary embodiments, one or more of the following steps may be performed to form and bond the distal tip on the end of an inner catheter:
1. Set a heat box to 325° F.±5° F. & 25 SCFH.
2. Trim the distal end of the inner catheter to 3±0.5 mm from the distal edge of outer catheter.
3. Insert a 0.020" diameter mandrel into distal end of the inner catheter (>2 cm.) Utilization of the mandrel controls the inside diameter and concentricity of all the tubing involved during the reflow process.
4. Place a heat shield over the inner catheter adjacent to the marker band (which is located proximal to the distal end of the inner catheter.)
5. Slide tube A onto the distal end of the inner catheter with a 2 mm overlap.
6. Place a RNF heat shrink tube over tube A and heat in heat box for 35-40 sec.
7. Skive the RNF tube with a razor blade, being careful not to cut through the RNF layer, and peel away the RNF layer.
8. Slide tube W onto tube A with a 1.75 to 2.00 mm overlap with tube A, making sure to leave a small gap (0.25 mm) between the proximal end of tube W and the distal end of the inner catheter. NOTE: This gap should close during the reflow process.
9. Place a RNF heat shrink tube over both tube A and Tube W (all layers) and heat for 35-40 sec.

10. Skive the RNF tube with a razor blade, being careful not to cut through the RNF layer, and peel away the RNF layer.
11. Trim distal tip to 7+1 mm from the distal edge of the inner catheter.

After the above reflow process, the following steps may be performed to create a taper on the distal tip:
1. Set the heat box to 325° F.±5° F. & 25 SCFH.
2. Insert a 0.020" diameter mandrel into distal end of catheter (>2 cm).
3. Place a RNF heat shrink tube over the distal tip assembly.
4. Starting at distal end of the RNF tube, heat ≤0.5 mm on to tube W for 2-5 sec.
5. Visually inspect under microscope to confirm taper on distal edge.

After the above taper process, the following steps may be performed to shape the distal tip:
1. Set the heat box to 230° F.±10° F.
2. Set air flow to 40+5 SCFH.
3. Slide the straight tip onto a shaping mandrel. Note that to create a 90 degree bend in the tip, a mandrel having a 105 degree bend is used since the tip material will relax back to about 90 degrees after the shaping process in complete.
4. Slide the tip up to a mandrel stop around the bend to 12 mm±0.5 mm from the end of the mandrel.
5. Place the tip and mandrel into the heat box for 3 mins±10 s. Start heating at tube A and slowly move toward the distal end of tube W.
6. Keep the mandrel in the tip until it cools.

In another embodiment similar to the construct shown in FIG. 17A, a 55 durometer Pebax tube with $BaSO_4$ additive is used as tube A, a 35 durometer Pebax tube is used as tube B, and a 25 durometer Pebax tube with Tungsten is used as tube W. A temperature approximately 25° F. higher may be needed to process tube A due to its higher durometer.

The shaped catheter tips disclosed herein created by layering or abutting different materials can offer improved bend profiles, transition from rigid to flexible in a gradient rather than abrupt changes which in turn can reduce kinking of the catheter tip, and can provide sharper bends in a shorter length of catheter tip in order to more easily navigate through tight bends in the vasculature.

Figures 21A, 21B, 21C:
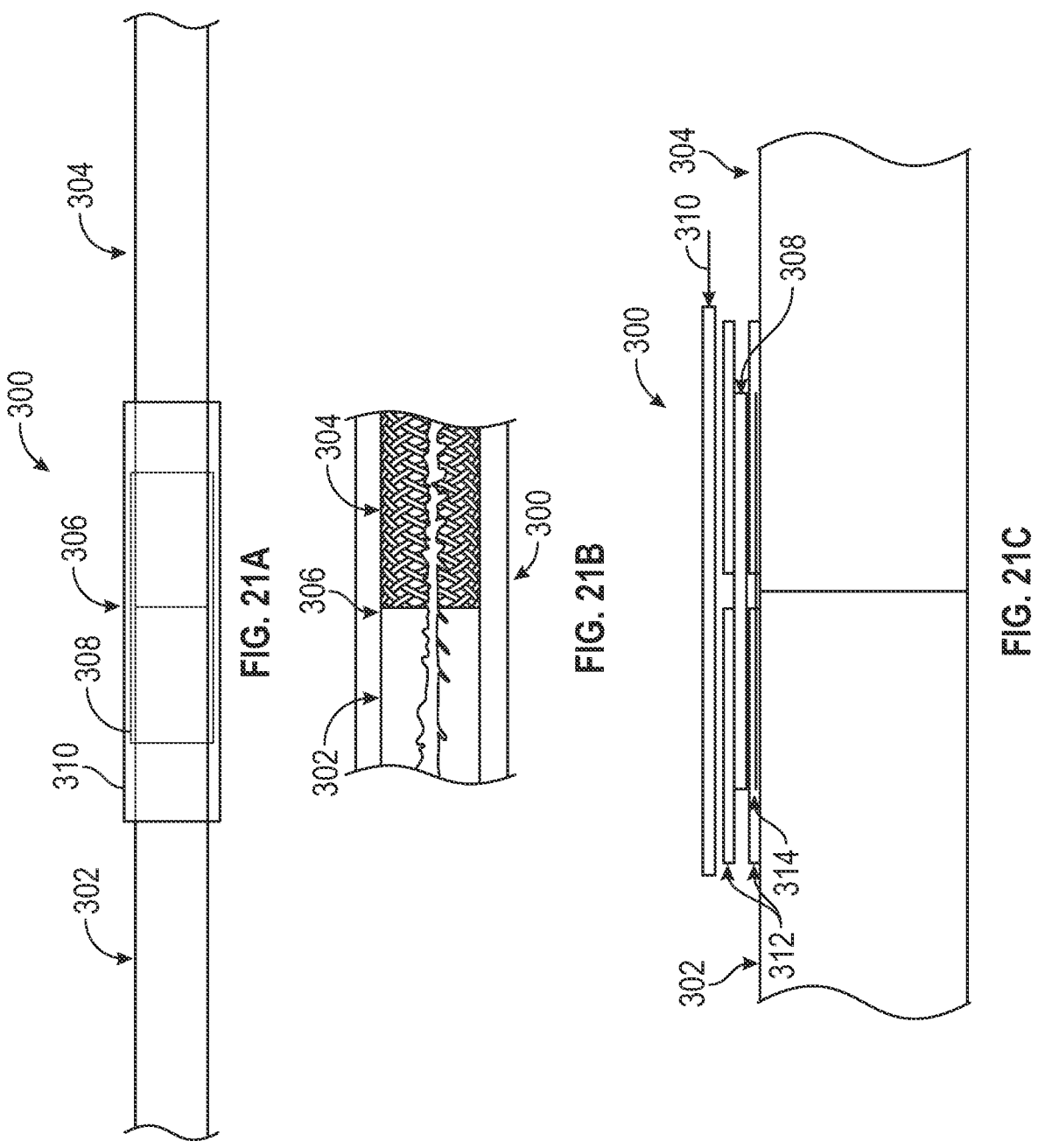
FIGS. 21A, 21B and 21C illustrate an exemplary manner in which a proximal outer catheter section can be secured to a distal outer catheter section.

In some embodiments, an outer catheter includes a proximal outer catheter section and a distal outer catheter section, such as proximal outer catheter section 116 and distal outer catheter section 118. The two sections may be secured to one another using a variety of techniques. FIGS. 21A-21C illustrate an exemplary manner in which proximal outer catheter section 302 is secured to distal outer catheter section 304 at location 306. The types of material used for the proximal and distal catheter sections may cause it to be difficult to reliably secure the two types of material directly together, such as at a butt joint between the two sections. For example, two dissimilar materials may be difficult to securely bond together in a manner that ensures they won't be pulled apart during use. For example, if one of the sections comprises a polyimide and the adjacent section comprises a PEBAX material, it may be difficult to reliably heat fuse the two sections together at a butt joint in a way that ensures the sections will not pull apart from one another when in use. FIGS. 21A-21C illustrate an embodiment in which one or more outer securing layers are used to secure (or at least more reliably secure) the proximal outer catheter section to the distal outer catheter section. FIGS. 21A-21C illustrate a portion of outer catheter 300 that includes proximal outer section 302, distal outer section 304, first overlay securing member 308, and optional second overlay securing member 310. FIG. 21B illustrates a braided material in each of the proximal and distal sections, joined at region 306, such as any of the those described herein.

FIG. 21C illustrates a magnified portion of an exemplary outer catheter 300, with proximal outer section 302 and distal outer section 304. The outer catheter 300 includes epoxy adhesive layers 312, the bottom of which is reinforced with one or more fibers 314 (e.g., Kevlar). First overlay securing member 308 is disposed atop the fiber reinforced bottom epoxy adhesive layer 312. A second epoxy adhesive layer is disposed atop member 308, and second overlay securing member 310 is disposed on top of the second adhesive layer.

The first securing member 308 may be sufficient to secure the proximal and distal sections, but using a second securing member 310 can provide added reinforcement to ensure the outer catheter sections do not come apart. In some exemplary embodiments members 308 and 310 may comprise polyethylene terephthalate ("PET").

In some embodiments the lengths of the first and second overlay securing members may be between 0.01 inches and 0.2 inches. In some embodiments the thicknesses of the first and second overlay securing members may be between 0.0001 inches and 0.001 inches.

FIGS. 21A-21C illustrate a catheter that includes axially adjacent outer catheter sections (e.g., 302, 304) that are secured (or at least more reliably secured) with one or more layers that are disposed radially outside the adjacent outer catheter sections, and that axially overlap the two adjacent sections. The adhesive layer(s) also are radially outside the two adjacent outer catheter sections, and axially overlap the adjacent outer catheter sections.

The portion of the exemplary outer catheter shown in FIGS. 21A-21C may be incorporated into any of the catheters herein.

As set forth herein, some of the catheters include an inflatable balloon. In any of the embodiments, a compression member can be used to create a compression bond that at affixes (or helps affix) the balloon end to a portion of the catheter. In this context, a compression bond deforms the balloon material and help maintain its position relative to a portion of the catheter. In this context, a compression bond can be thought of as a mechanical constraint.

Traditionally common ways to affix a balloon to a catheter is using heat bonding, although solvent or adhesive may also be used. Silicone, however, cannot be affixed using any of these methods. Compression bonding one or both ends of a balloon to a portion of the catheter can thus facilitate securing balloons comprising a silicone material. Silicon has superior properties, yet is not used because it is challenging to bond. Compression bonding thereby facilitates bonding of balloons comprising a silicone material to a catheter.

Any of the collars herein may be used to implement a compression bond, and the collar may take the form of a small annular member, and may be disposed on the distal and proximal ends of the balloon. The collar need not be secured to any other portion of the catheter except the balloon outer surface. Collar as used herein may be used interchangeably with the support sheaths herein.

FIGS. 22-25 illustrate exemplary balloon bonding techniques, any of which can be implemented in any of the catheters herein. Suitable disclosure herein related to any of the embodiments in FIGS. 22-25 can be incorporated into the embodiments in FIGS. 22-25 even if not specifically indicated herein.

Figures 22, 23:
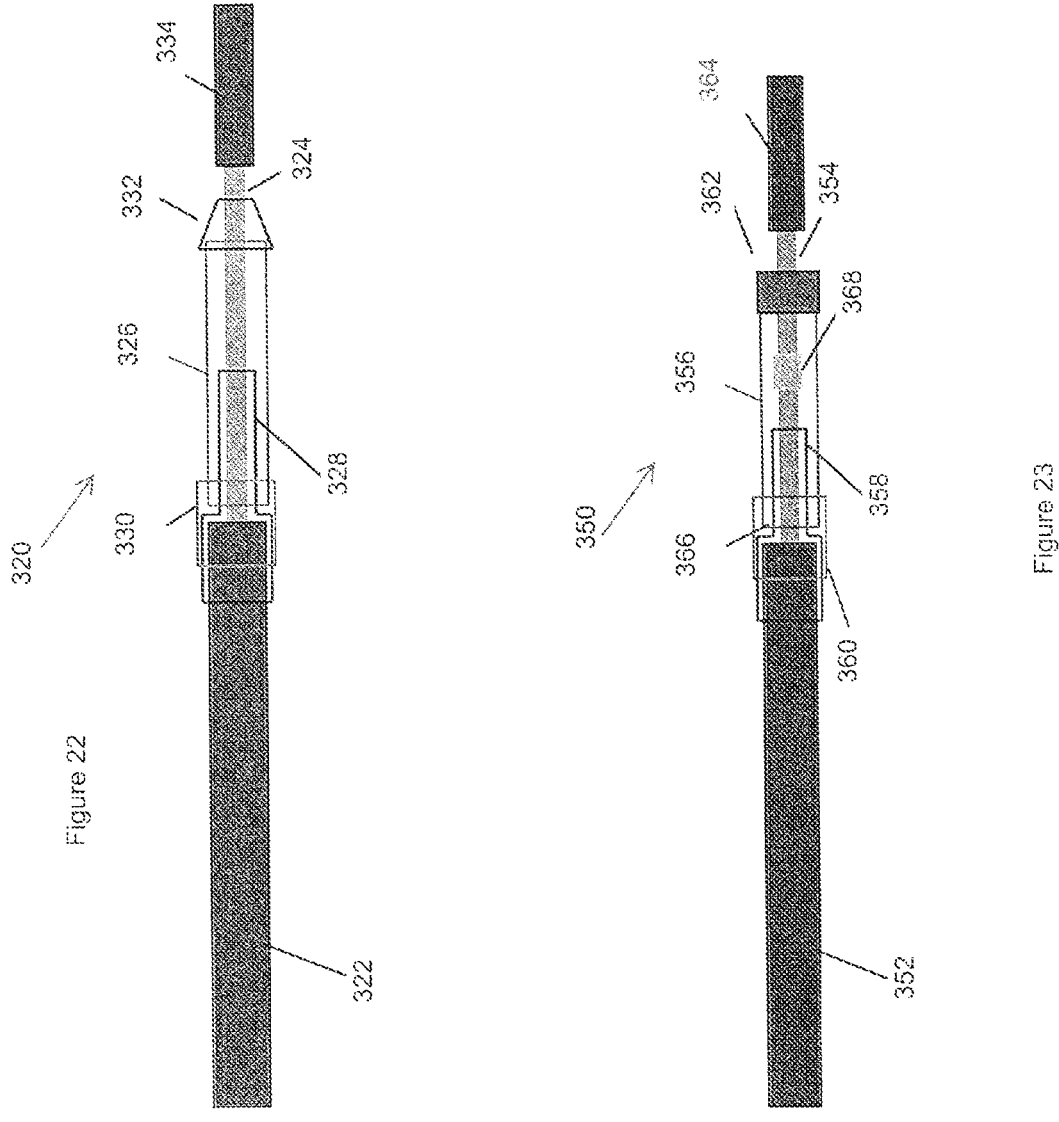
FIG. 22 illustrates a manner in which a balloon may be secured to a balloon catheter.
FIG. 23 illustrates a manner in which a balloon may be secured to a balloon catheter.

FIG. 22 illustrates exemplary catheter 320, which includes outer catheter 322, inner catheter 324, balloon 326, adaptor 328, and distal tip 334. Proximal collar 330 can create a compression bond at the proximal end of balloon 326, while distal collar 332 may form a compression bond at the distal end of balloon 326. Catheter 320 may be modified according to any other embodiment herein (e.g., adaptor 328 may be an inner adaptor).

FIG. 23 illustrates exemplary catheter 350, which includes outer catheter 352, inner catheter 354, balloon 356, adaptor 358, and distal tip 364. Proximal collar 360 may create a compression bond at the proximal end of balloon 356, while distal collar 362 may form a compression bond at the distal end of balloon 356. Adhesive 366 is also shown, which may help create friction rather than form adhesive bonds, which is discussed elsewhere herein. Catheter 350 can also include marker band 368, disposed within balloon 356 and secured to inner catheter 354. Catheter 350 may be modified according to any other embodiment herein (e.g., adaptor 360 may be an inner adaptor).

Figures 24, 25:
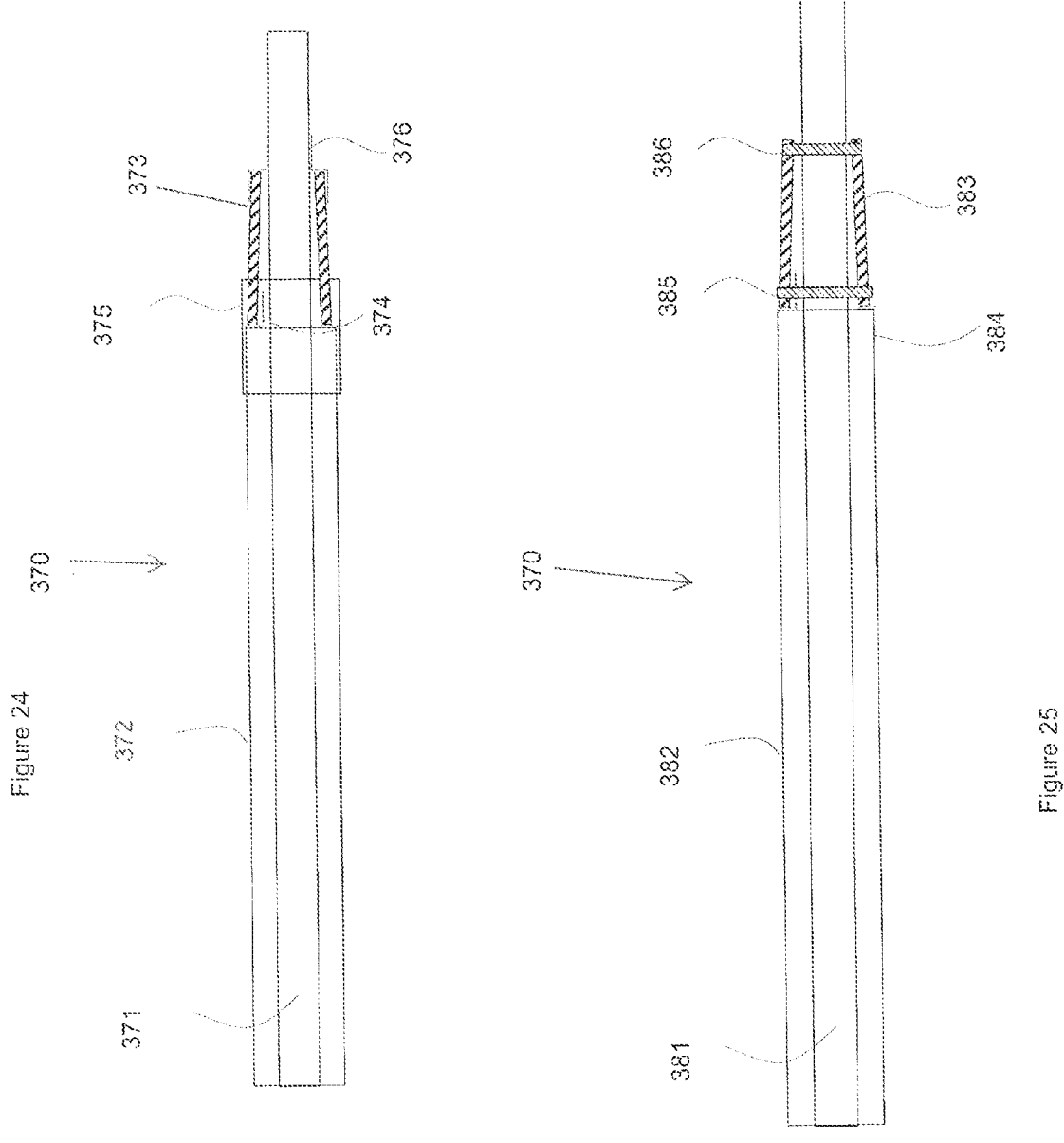
FIG. 24 illustrates a manner in which a balloon may be secured to a balloon catheter.
FIG. 25 illustrates a manner in which a balloon may be secured to a balloon catheter.

FIG. 24 illustrates a portion of exemplary catheter 370, which includes outer catheter 371, inner catheter 372, balloon 373, adaptor 374, support sheath/collar 375, and distal collar 376. Proximal collar 375 may create a compression bond at the proximal end of balloon 373, while distal collar 376 may form a compression bond at the distal end of balloon 373. Distal collar 376 overlaps balloon 373 and inner catheter 371.

FIG. 25 illustrates a portion of exemplary catheter 380, which includes outer catheter 382, inner catheter 381, balloon 383, adaptor 384, proximal annular collar 385, and distal annular collar 386. Proximal collar 385 may create a compression bond at the proximal end of balloon 383, while distal collar 386 may form a compression bond at the distal end of balloon 383. In FIG. 25, the collars are annular in form, and do not engage catheter surfaces other than the balloon. The proximal and distal collars in FIGS. 24 and 25 may be used interchangeably with each other (e.g. one collar that only interfaces the balloon, with one collar that overlaps the outer or inner shaft).

Any of the balloons herein may comprise a latex, a urethane, a polyurethane, and/or a nylon material.

Any of the balloons herein that include a silicone material may comprise a silicone co-polymer, may include more than one silicones, and/or may include latex and a silicone.

Any of the adaptors herein may comprise PET, or consist essentially of PET. Any of the collars and sheaths herein may comprise PET, or consist essentially of PET.

Any of the catheters herein can be used in any method or any one or more steps described in U.S. Pat. No. 9,844,383, which is fully incorporated by reference herein for all purposes.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the disclosure. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the FIGS. is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present disclosure.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the disclosure as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the disclosure as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" or "disclosure" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A balloon catheter, comprising:
an outer elongate shaft having a wall thickness that is less than 0.0035 inches;
an inner elongate shaft with a delivery lumen therein, the inner elongate shaft within the outer elongate shaft having a section that extends distally beyond the outer elongate shaft, the inner elongate shaft having a wall thickness that is less than 0.0035 inches;
an adapter secured to a distal region of the outer elongate shaft, the adapter having a stepped down distal region extending distally beyond the outer elongate shaft, the distal region of the adapter having an outer surface disposed radially inward relative to an outer surface of a distal end of the outer elongate shaft, the adapter having a proximal region having an inner surface disposed radially outward relative to the outer surface of the distal end of the outer elongate shaft, wherein the adapter has a length from 2 mm to 25 mm;
an inflatable balloon with a proximal end;
a proximal collar radially outside of the proximal end of the inflatable balloon, the proximal collar compressing the proximal end of the inflatable balloon between the proximal collar and the outer surface of the distal region of the adapter, wherein an inner surface of the proximal end of the inflatable balloon is disposed radially inward relative to the outer surface of the distal end of the outer elongate shaft,
wherein the outer elongate shaft does not include a step-down in a region proximal to the proximal end of the inflatable balloon to the distal end of the outer elongate shaft;
the inflatable balloon having a distal end stabilized relative to the section of the inner elongate shaft that extends distally beyond the outer elongate shaft, the distal end of the inflatable balloon having the inner surface that is disposed radially inward relative to the outer surface of the distal end of the outer elongate shaft,
the outer elongate shaft and the inner elongate shaft forming an inflation lumen that is in communication with the inflatable balloon to allow fluid to be advanced through the inflation lumen and into an internal volume of the inflatable balloon to inflate the inflatable balloon,
wherein the inflatable balloon along an entirety of its length is disposed substantially at or below an outer diameter of the outer elongate shaft when in an unexpanded configuration.

2. The balloon catheter of claim 1, further comprising a distal collar radially outside of the distal end of the inflatable balloon, the distal collar compressing the distal end of the inflatable balloon between the distal collar and the section of the inner elongate shaft that extends distally beyond the outer elongate shaft.

3. The balloon catheter of claim 2, wherein the distal collar is a heat shrink material that compresses the distal end of the inflatable balloon.

4. The balloon catheter of claim 2, wherein the distal collar has a thickness from 0.003 mm to 0.05 mm.

5. The balloon catheter of claim 2, wherein the distal collar has a length from 0.1 mm to 10 mm.

6. The balloon catheter of claim 2, wherein the distal collar comprises a polymeric material.

7. The balloon catheter of claim 1, wherein the adapter is secured to an outer surface of the distal region of the outer elongate shaft.

8. The balloon catheter of claim 7, wherein the adapter comprises a step from a first region to a second region, the first region extending radially outward further than the second region.

9. The balloon catheter of claim 1, wherein the adapter is secured to an inner surface of the distal region of the outer elongate shaft.

10. The balloon catheter of claim 9, wherein the adapter comprises a step from a first region to a second region, the first region extending radially outward further than the second region.

11. The balloon catheter of claim 1, wherein the adapter has a thickness from 0.0016 mm to 0.025 mm.

12. The balloon catheter of claim 1, wherein the adapter has a thickness that is no more than 15% of a wall thickness of the distal end of the outer elongate shaft.

13. The balloon catheter of claim 1, wherein the distal region of the adapter has a wall thickness less than 0.01 mm.

14. The balloon catheter of claim 1, wherein the adapter comprises a polymeric material.

15. The balloon catheter of claim 1, wherein the proximal collar is a heat shrink material that compresses the proximal end of the inflatable balloon.

16. The balloon catheter of claim 1, wherein the proximal collar has a thickness from 0.003 mm to 0.05 mm.

17. The balloon catheter of claim 1, wherein the proximal collar has a length from 1 mm to 10 mm.

18. The balloon catheter of claim 1, wherein the proximal collar comprises a polymeric material.

19. The balloon catheter of claim 1, wherein the inflatable balloon is elastic.

20. The balloon catheter of claim 19, wherein the inflatable balloon comprises a silicone material.

21. The balloon catheter of claim 20, wherein the inflatable balloon consists essentially of a silicone material.

22. The balloon catheter of claim 1, further comprising an adhesive disposed radially between the proximal end of the inflatable balloon and an outer surface of the distal region of the adapter.

23. The balloon catheter of claim 1, further comprising an adhesive disposed radially between the distal end of the inflatable balloon and the section of the inner elongate shaft that extends distally beyond the outer elongate shaft.

24. The balloon catheter of claim 1, wherein the inflatable balloon, in the unexpanded configuration, is disposed at or below the outer diameter of the outer elongate shaft.

25. The balloon catheter of claim 1, wherein the inner surface of the proximal end of the inflatable balloon is at least 0.001 inches below the outer surface of the outer elongate shaft.

26. The balloon catheter of claim 1, wherein the inner surface of the distal end of the inflatable balloon is at least 0.001 inches below the outer surface of the outer elongate shaft.

27. The balloon catheter of claim 1, wherein the adapter has a thickness from 0.003 mm to 0.015 mm.

* * * * *